(12) United States Patent
Hughes

(10) Patent No.: US 11,684,508 B2
(45) Date of Patent: Jun. 27, 2023

(54) DEVICE FOR CATCHING URINE SAMPLE

(71) Applicant: Samantha Hughes, Auckland (NZ)

(72) Inventor: Samantha Hughes, Auckland (NZ)

( * ) Notice: Subject to any disclaimer, the term of this patent is extended or adjusted under 35 U.S.C. 154(b) by 146 days.

(21) Appl. No.: 17/085,546

(22) Filed: Oct. 30, 2020

(65) Prior Publication Data

US 2022/0133523 A1 May 5, 2022

(51) Int. Cl.
| | |
|---|---|
| *A61F 5/451* | (2006.01) |
| *A61F 5/44* | (2006.01) |
| *A61B 10/00* | (2006.01) |
| *A61F 5/449* | (2006.01) |
| *A61G 9/00* | (2006.01) |
| *A47K 11/04* | (2006.01) |
| *A47K 11/12* | (2006.01) |
| *A47K 13/06* | (2006.01) |
| *A47K 11/06* | (2006.01) |
| *A47K 17/02* | (2006.01) |
| *B01L 3/00* | (2006.01) |

(52) U.S. Cl.
CPC ............ *A61F 5/451* (2013.01); *A61B 10/007* (2013.01); *A61F 5/4404* (2013.01); *A61F 5/449* (2013.01); *B01L 3/502* (2013.01); *A47K 11/04* (2013.01); *A47K 11/06* (2013.01); *A47K 11/12* (2013.01); *A47K 13/06* (2013.01); *A47K 17/02* (2013.01); *A61F 5/4408* (2013.01); *A61G 9/006* (2013.01)

(58) Field of Classification Search
CPC ........ A61F 5/451; A61F 5/4404; A61F 5/449; A61F 5/4408; A61B 10/007; A47K 11/04; A47K 11/06; A47K 11/12; A47K 13/06; A47K 17/02; A61G 9/006
See application file for complete search history.

(56) References Cited

U.S. PATENT DOCUMENTS

| | | | | |
|---|---|---|---|---|
| 2,662,229 | A * | 12/1953 | Wenkstern | A47K 11/06 4/476 |
| 6,957,612 | B2 * | 10/2005 | Conlee | A47B 23/002 108/43 |
| 2007/0148409 | A1 * | 6/2007 | Rios | C09J 7/25 428/167 |
| 2016/0045087 | A1 * | 2/2016 | Pratcher | A47K 11/06 4/237 |
| 2018/0070738 | A1 * | 3/2018 | Burns | A47D 9/02 |
| 2018/0247564 | A1 * | 8/2018 | Decker | A47K 11/06 |
| 2020/0078207 | A1 * | 3/2020 | Parr | A61F 5/4404 |
| 2020/0237116 | A1 * | 7/2020 | Yabuuchi | A47D 15/006 |

* cited by examiner

*Primary Examiner* — Susan S Su
*Assistant Examiner* — Ted Yang
(74) *Attorney, Agent, or Firm* — Franklin & Associates International Inc; Matthew F. Lambrinos

(57) ABSTRACT

A urine collection device for collecting a sterile urine sample. The urine collection device may include a seat portion supported by a seat base. The portion includes a backrest and a saddle that projects from the seat portion. The saddle has an opening to a collection element that includes a cup mount to locate a urine collection cup within the collection element.

17 Claims, 37 Drawing Sheets

DEVICE FOR CATCHING URINE SAMPLE

TECHNICAL FIELD

This present technology relates to a device for collecting a urine sample. The device is particularly suited for collecting urine samples from babies and toddlers but could otherwise be used to collect urine samples from children and adults with physical disabilities.

BACKGROUND

Sterile urine samples are typically required to diagnose urinary tract infections and other health problems, particularly problems affecting the kidneys. Diagnosis relies on obtaining an uncontaminated sample which has to be a 'flying stream' of urine caught in a sterile collection cup, without coming into contact with any contaminating factors, such as fingers making contact with the inside area of the sterile collection cup, or the urine being collected making contact with the skin surrounding the urethra before being collected. A contaminated sample may be unable to be properly analysed or may lead to misdiagnosis, resulting in unnecessary or delayed treatments. However, it can be difficult to easily obtain sterile urine samples from incontinent people, such as pre-continent children for example, and from people with severe physical disabilities that make it difficult to sit on a toilet.

For example, difficulties often arise when obtaining a urine sample from a pre-continent child (a child who is not yet 'potty trained', who is typically below the age of 2 years old). Because the child cannot pass urine voluntarily or in a timely manner, several different methods are currently used to collect a sterile sample of urine from pre-continent children.

One option for urine sample collection is to use the 'catch' method in which an adult (typically the parent) attempts to catch a 'flying stream' of urine by sitting the child on their lap whilst holding a sterile collection cup in position. The adult will also need to keep the child calm and still, whilst paying attention to whether the child is urinating so that they can catch the mid-stream sample with the cup in their hands. This method is time intensive and frustrating for both parent and child because they can be waiting a long time for the child to urinate. The sample can also be easily missed or contaminated, and it is a messy experience for the parent that typically involves getting urine splattered on their hands as part of the process.

Another option is to use the catheterisation method, in which a catheter is inserted into the bladder to collect an uncontaminated sample. Although effective, the procedure is traumatic for the baby and the parent. Catheterisation is commonly used for adults also and can be uncomfortable for the patient.

Yet another option is to use the bag collection method, which involves adhering a liquid impervious bag to the child's genitals and into which the child urinates. However, due to the requirement for a sterile sample not to be contaminated by contact with external skin, this method is often ineffective.

Therefore, disadvantages are associated with each method for collecting a urine sample and the overall process is often stressful and challenging for the child and parents and can also contribute to workplace stress for the nursing staff and clinicians.

An object of the present technology is to provide a device for capturing a urine sample that goes at least some way towards overcoming the problems associated with known urine collection systems or to at least provide a useful alternative.

SUMMARY

In a first aspect, the present technology provides a urine collection device for collecting a urine sample, the device comprising a seat portion supported by a seat base, the seat portion comprising a backrest and a saddle that projects from the seat portion, wherein the saddle comprises a saddle opening that provides fluid access to a collection element, the collection element comprising a cup mount to locate a urine collection cup within the collection element.

In some forms, the collection element comprises a cup receiving opening defined by a rim, the cup receiving opening being shaped and dimensioned to receive at least a portion of a urine collection cup and the rim comprising the cup mount to engage with the urine collection cup to hold the cup within the collection element. Optionally, the collection element comprises one or more side walls that slope toward the cup receiving opening.

In some forms, the backrest reclines rearwardly from the seat base. Optionally, the seat base comprises a front edge that connects with the seat portion, and the seat portion reclines from the front edge of the seat base such that a rear surface of the seat portion generally opposes an upper surface of the seat base.

Optionally, the backrest comprises a lumbar support.

In some forms, the seat portion comprises a hollow to receive at least a portion of a patient's buttocks, the hollow being located between the backrest and the saddle. Optionally, the hollow is at least partially defined by one or more curved side walls. Optionally, the hollow comprises a bottom surface surrounded by one or more side walls to collect fecal matter and urine overflow.

In some forms, the backrest comprises a central portion located between two side portions, each of the side portions terminating at a respective left or right side of the seat portion, and wherein the backrest is angled or curved between the left and right sides to form a substantially trough-like profile, in which the central portion of the backrest is rearward of the left and right sides. Optionally, the seat portion comprises a pair of leg wells to receive a patient's legs therein, each of the leg wells extending along the seat portion on either side of the saddle. Optionally, the saddle comprises a substantially arcuate frame comprising an arched central portion located between a pair of spaced apart saddle side walls, and wherein one of the pair of leg wells extends between a respective one of the pair of saddle side walls and a respective one of the left and right sides of the seat portion.

In some forms, the saddle comprises a pair of spaced apart side walls located on either side of the saddle opening, and wherein the collection element is adjustably locatable in a space between the side walls. Optionally, the collection element comprises a shield connected to a supporting base and wherein a cup stand projects from a rear surface of the shield and wherein the cup mount is provided on the cup stand.

In some forms, the urine collection device comprises a retaining member that spans across the seat portion to retain the patient on the device. Optionally, the retaining member is detachably attachable to the seat portion.

In some forms, the retaining member comprises a substantially T-shaped three-point harness comprising a first end that attaches to one side of the backrest, a second end that attaches to the other side of the backrest, and a third end that attaches to the saddle.

In some forms, the seat portion and at least one of the ends of the retaining member each comprise at least one engagement feature to detachably attach the retaining member to the seat portion. Optionally, the at least one engagement feature of the seat portion comprises an opening, recess, or hook to engage with a complimentary engagement feature of the retaining member. Optionally, the engagement feature comprises a magnetic region such that the retaining member detachably attaches to the seat portion by a magnetic connection.

In some forms, at least one of the first and second ends of the retaining member comprises a magnetic region and wherein a rear surface of the seat portion comprises a magnetic region to which the retaining member may be attached. Optionally, at least one of the first and second ends of the retaining member is insertable through an opening provided in a respective side of the seat portion and is detachably attachable to the magnetic region on the rear surface of the seat portion.

In some forms, the retaining member comprises silicone and one or more magnets are located beneath an outer silicone surface of the retaining member.

In some forms, the third end of the harness comprises a magnetic region and the saddle comprises a magnetic region to attach to the third end. Optionally, the magnetic region is located on an upper surface of the saddle.

In some forms, the magnetic region of the seat portion comprises one or more magnets that are embedded within the seat portion or that are covered or over-moulded with a polymer.

In some forms, the magnetic region of the saddle comprises one or more magnets that are embedded within the saddle or that are covered or over-moulded with a polymer.

In some forms, the seat base comprises a non-slip lower surface. Optionally, the non-slip lower surface is textured or tacky.

In some forms, the seat base comprises a pair of spaced apart, arcuate channels that extend from a left side of the seat base to a right side of the seat base to position the seat base on the thighs of an adult when the device is in use.

Unless the context clearly requires otherwise, throughout the description and the claims, the words "comprise", "comprises", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The present technology consists in the foregoing and also envisages constructions of which the following gives examples only.

BRIEF DESCRIPTION OF THE DRAWINGS

Preferred forms of the present technology will now be described by way of example and with reference to the accompanying drawings, in which.

DETAILED DESCRIPTION OF PREFERRED EMBODIMENTS

The present technology is further described with reference to the following examples. It will be appreciated that the present technology as claimed is not intended to be limited in any way by these examples.

As exemplified by embodiments shown in FIGS. 1 to 33a, the present technology relates to a urine collection device 1000 for collecting sterile urine samples. The device 1000 is in the form of a chair or seat, preferably a reclining chair/seat, and can be used to collect urine samples from incontinent people, such as young children, elderly people and severely disable people. The device 1000 is particularly suitable for collecting a urine sample from a pre-continent child, such as a child aged up to about two years old. The device 1000 is usable with a removable and replaceable sterile urine collection cup 2000 that is supported by the device in a position that captures a flying stream or urine from the patient. A flying stream of urine is one in which the urine stream flows through the air and reaches the cup 2000 without touching another surface between being ejected from the patient and being received by the cup. This form of urine stream is less likely to be contaminated and will therefore be better able to provide accurate information when analysed.

The urine collection device 1000 comprises a seat comprising a seat portion 1100 supported by a seat base 1200. In some forms a support 1205, such as a rib, post, or solid form for example, may be provided between the seat portion and seat base. The seat portion 1100 comprises a front surface 1101, a rear surface 1102, and first and second sides 1103a, 1103b. The seat portion 1100 comprises a backrest 1110 for supporting a patient's back during use. In preferred forms, the backrest 1110 reclines rearwardly from the seat base 1200, but in other forms, the backrest may be substantially upright. In some forms, the backrest 1110 is reclined from a front edge 1210 of the device 1000 toward a rear edge 1111 of the backrest. Optionally, the device 1000 also comprises a retaining member 1170 that is attachable to the seat to retain a patient on the seat portion 1100 and to help prevent the patient falling or moving off the seat prematurely.

In some forms, as shown in FIGS. 1, 3, 3a, 5 and 7 for example, the seat base 1200 comprises a front portion or edge 1210 that connects with the seat portion 1100. The seat portion 1100 reclines from the front portion/edge 1210 of the seat base such that the rear surface 1102 of the seat portion generally opposes an upper surface 1201 of the seat base. In other forms, the seat portion 1100 may be supported by a support member 1205, extending between the base 1200 and seat portion 1100, and held in a reclined position. In some forms, the seat portion forms an acute angle relative to the seat base. In some forms, the angle is between about 15 degrees and about 70 degrees, such as between about 20 degrees and about 40 degrees, and optionally about 37 degrees.

Figure 1:
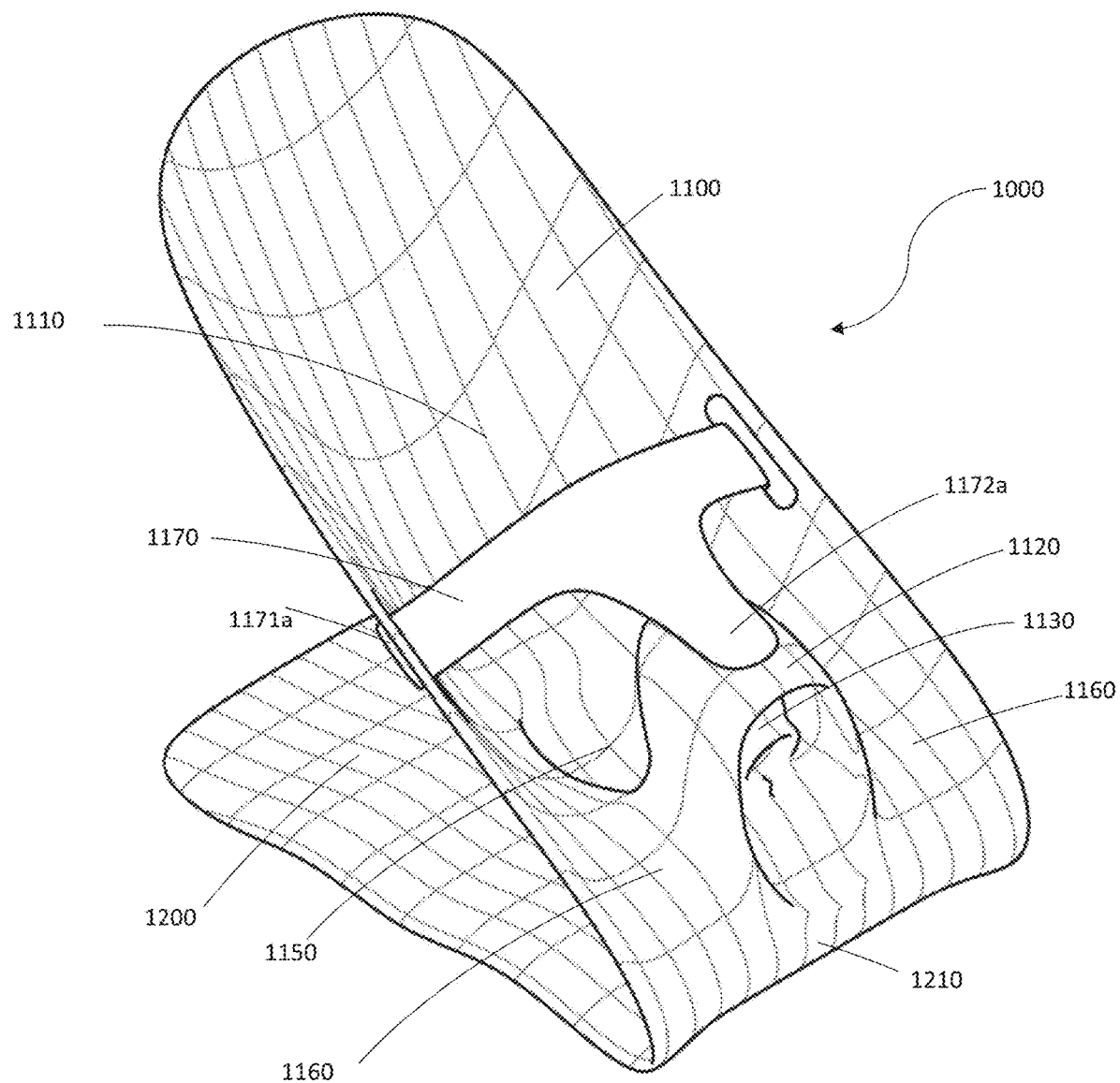
FIG. 1 is an isometric view of one form of device of the present technology that comprises a seat comprising a seat portion and a seat base and that also comprises an operational retaining member.
Figure 2:
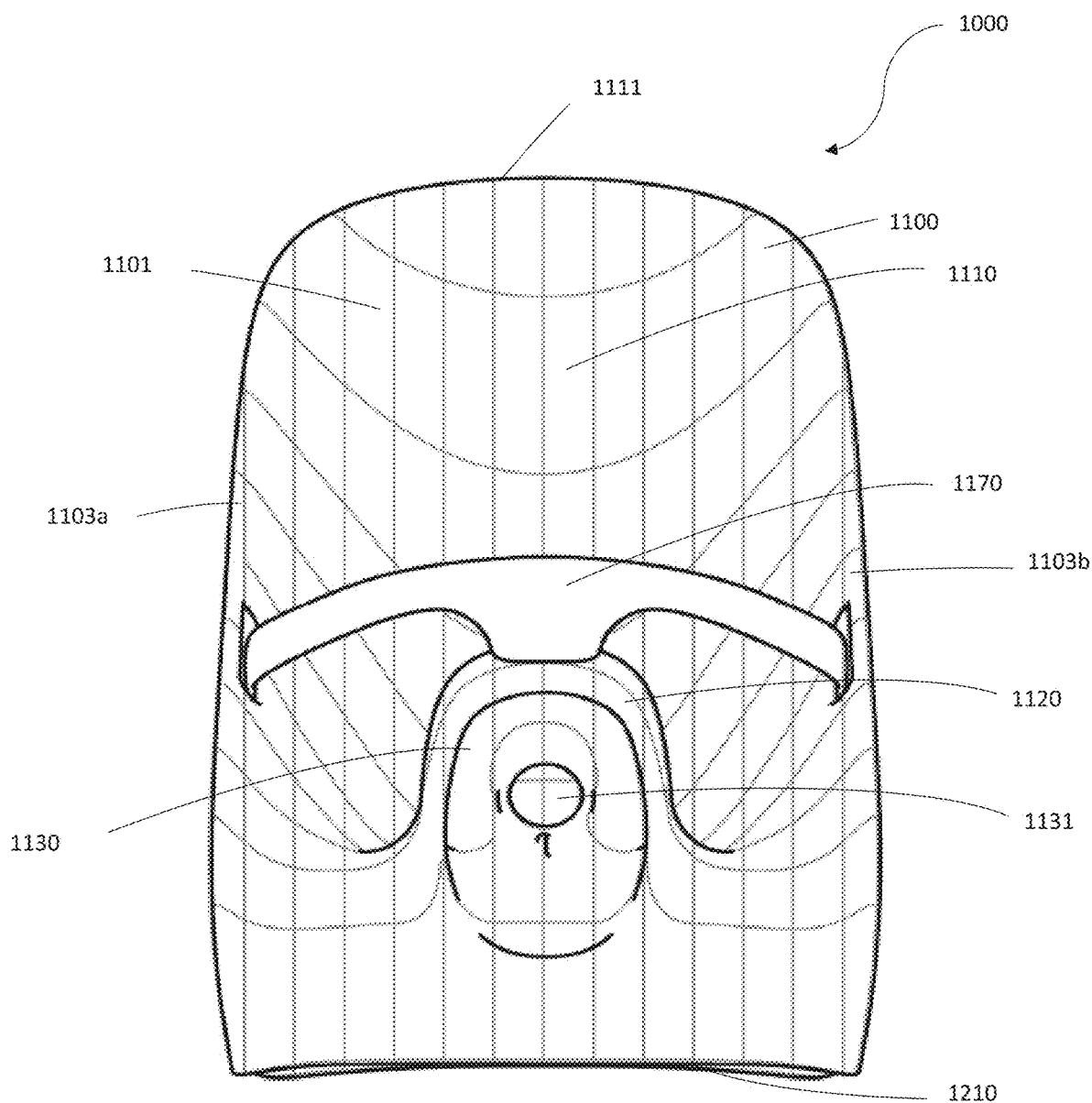
FIG. 2 is a front view of the seat assembly shown in FIG. 1.
Figure 5:
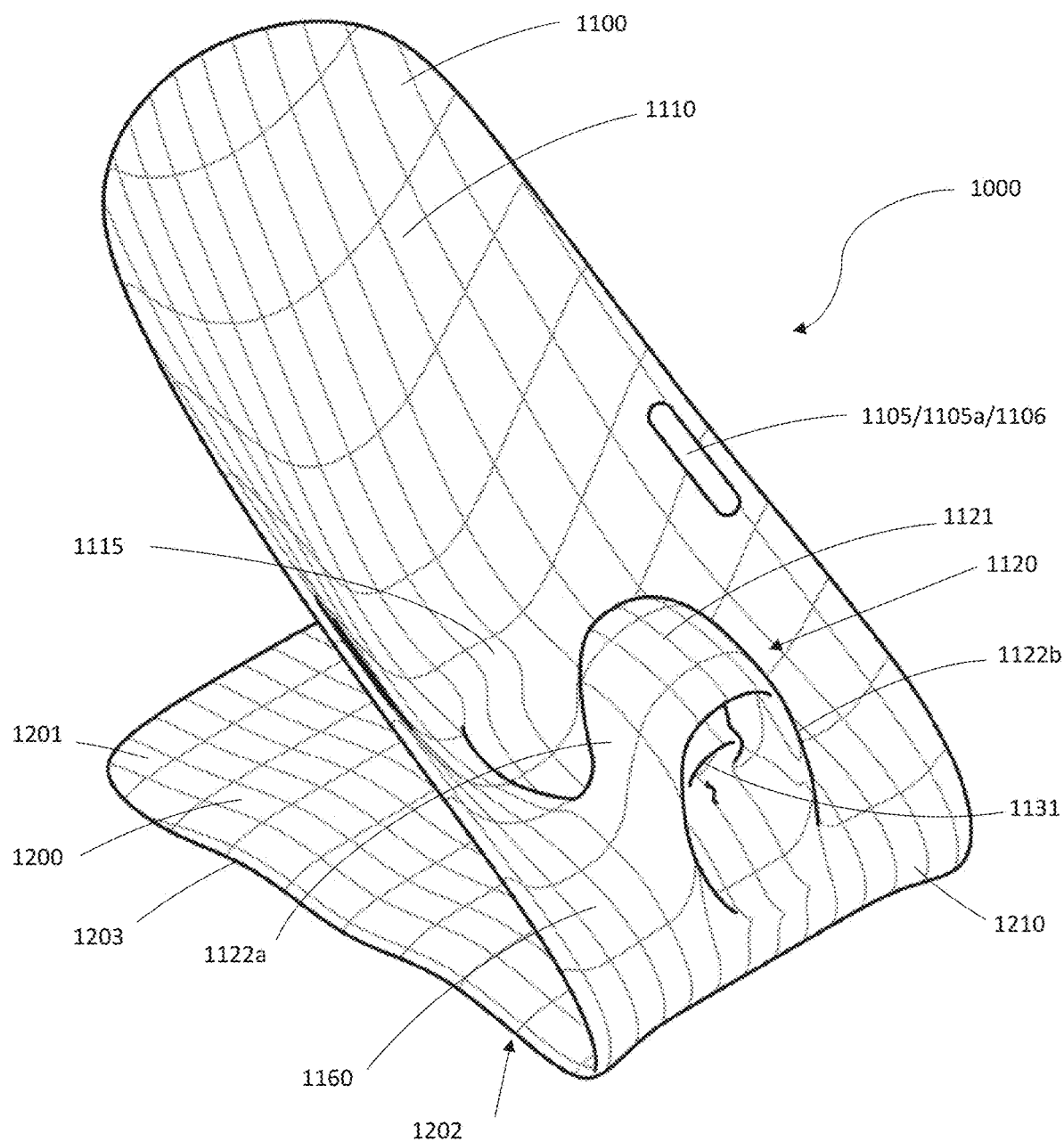
FIG. 5 is an isometric view of the device of FIG. 1, but without a retaining member, and in which openings on each side of the backrest may be used as handles.
Figure 6:
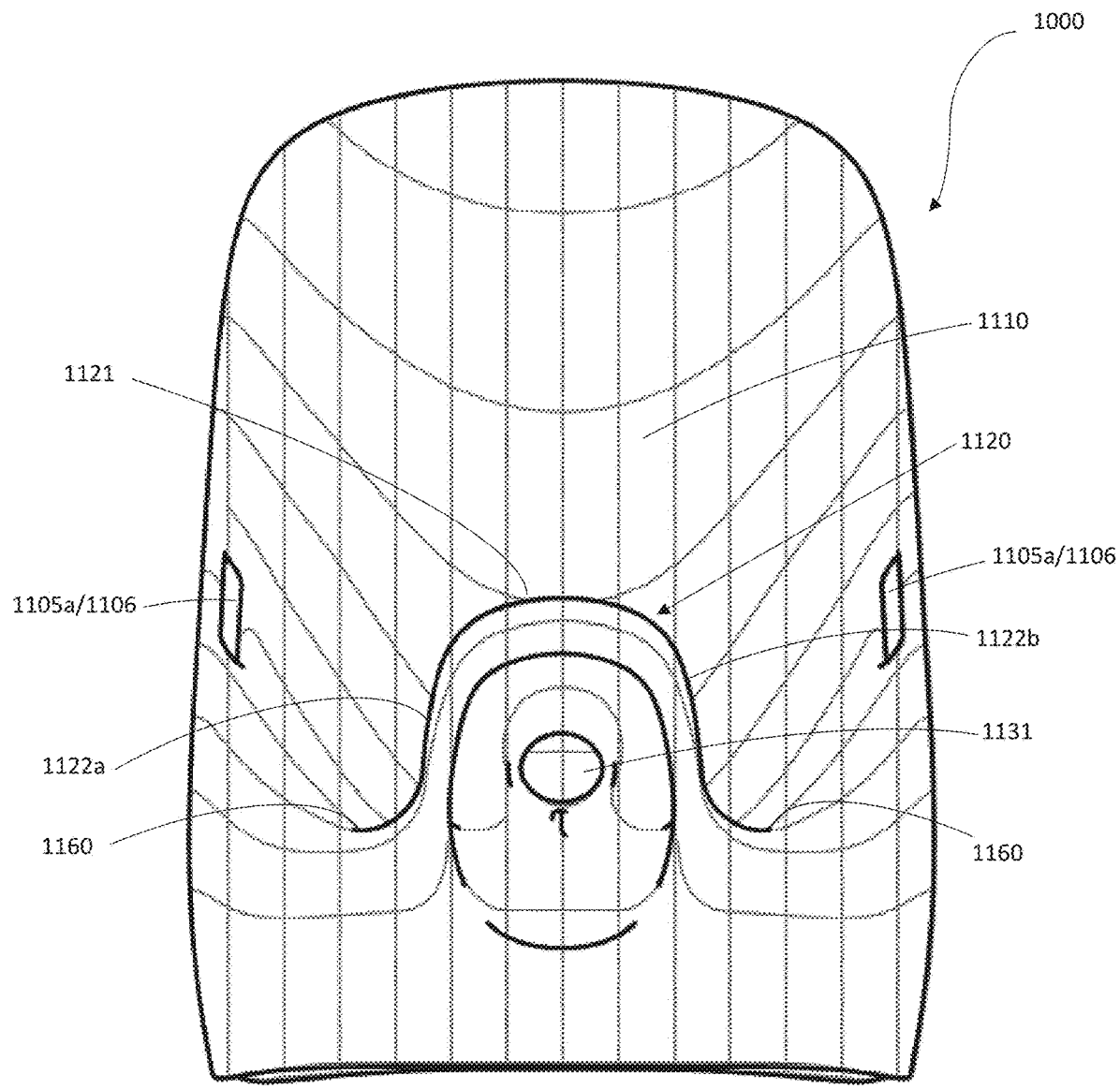
FIG. 6 is a front view of the device of FIG. 5.
Figure 7:
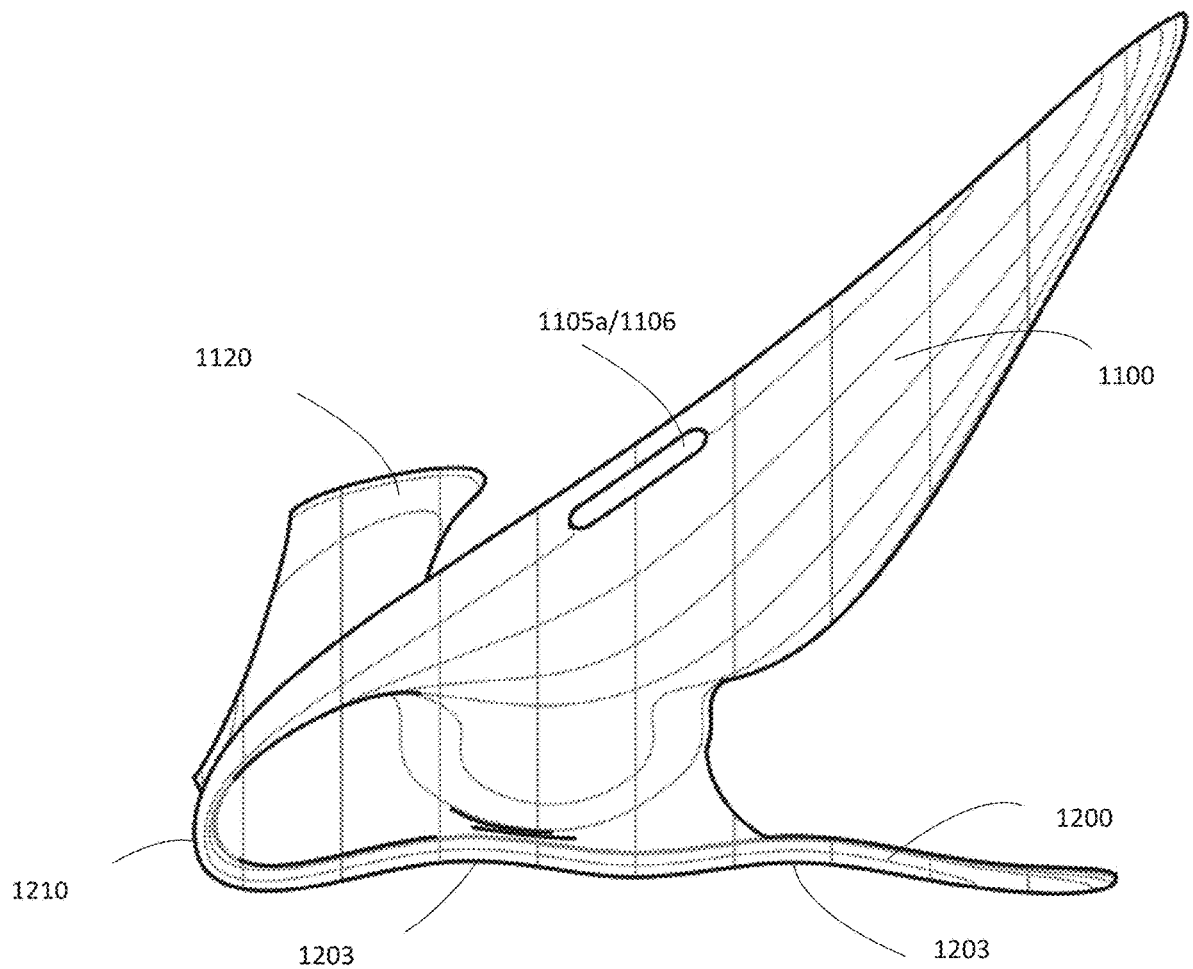
FIG. 7 is a side view of the device of FIG. 5.

The device/chair 1000 also comprises a saddle 1120 that projects from the front surface 1101 of the seat portion 1100, as shown for example in FIGS. 1, 5 and 7. In some forms, the saddle 1120 is located below the backrest 1110. The saddle 1120 is configured to be located between a patient's legs and comprises an opening 1124 that is, in use, located in front of the patient's genitals. The saddle 1120 helps to locate and retain a patient on the seat portion 1100. The device also comprises a collection element 1130 into which urine from the patient is directed to be received and contained by a sterile urine collection cup 2000 located within the element 1130. In embodiments shown in FIGS. 1 to 8, 11, and 15 to 19 for example, the saddle opening 1124 provides fluid access to the collection element and to a collection cup, when located within the collection element. In these forms, the collection element 1130 is located within the saddle 1120.

The saddle 1120 may be of any suitable shape to position the patient comfortably on the device and to help align the patient's genitals with the collection element 1130 located within the saddle. In some forms, the saddle 1120 comprises a substantially arcuate frame comprising an arched central portion 1121 located between a pair of side walls of the saddle 1122a, 1122b. Although the central portion 1121 may be substantially arched, a central region of the central portion 1121 may be curved to provide a peak or may be substantially flat. The central portion 1121 may comprise a gripping region for the patient to hold onto or it may comprise a visual feature for the patient to look at, such as appealing imagery. In other forms, the central portion 1121 may comprise a display mount for mounting a removable visual display, such as an electronic device having a display screen for displaying appealing content to the patient. For example, the electronic device may be a cellular phone or electronic tablet or notebook.

Figure 3:
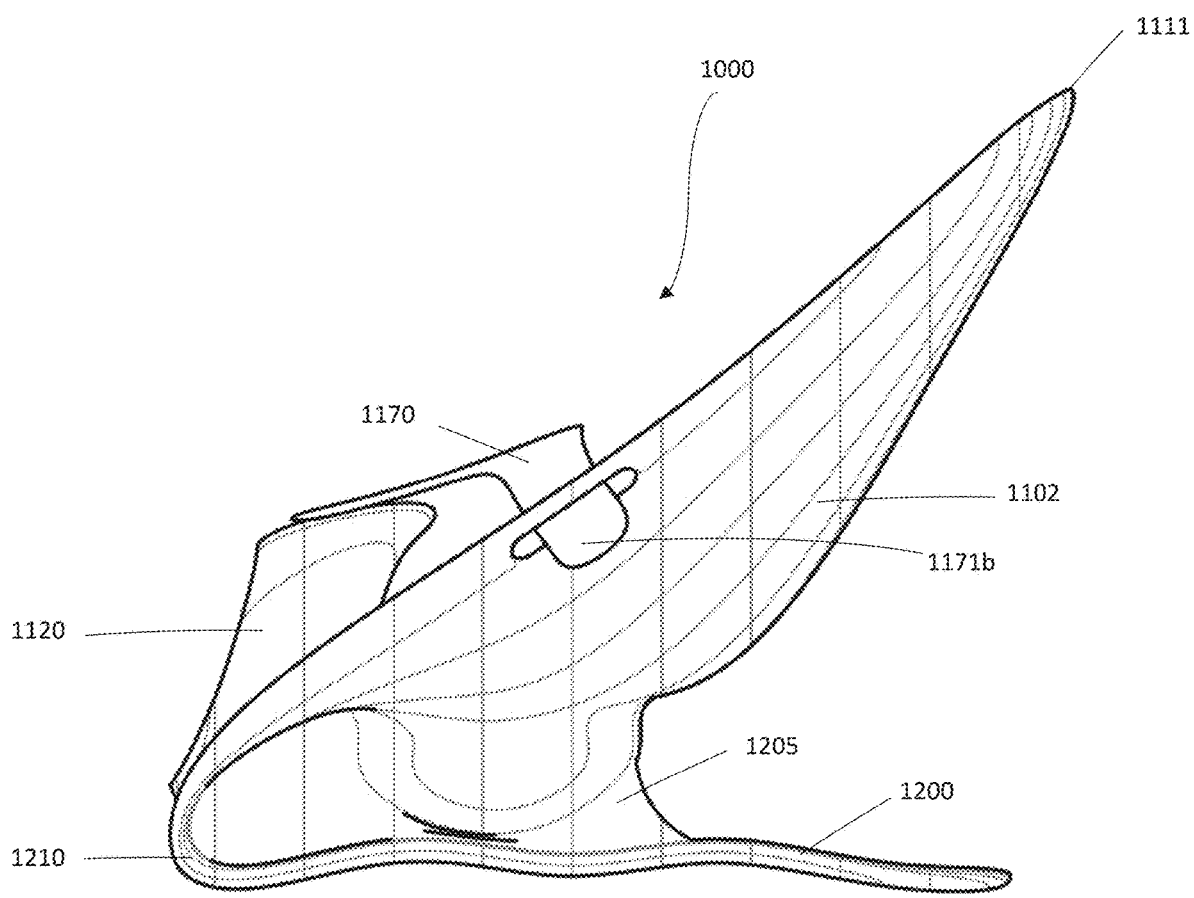
FIG. 3 is a side view of the seat assembly shown in FIG. 1.
Figure 3A:
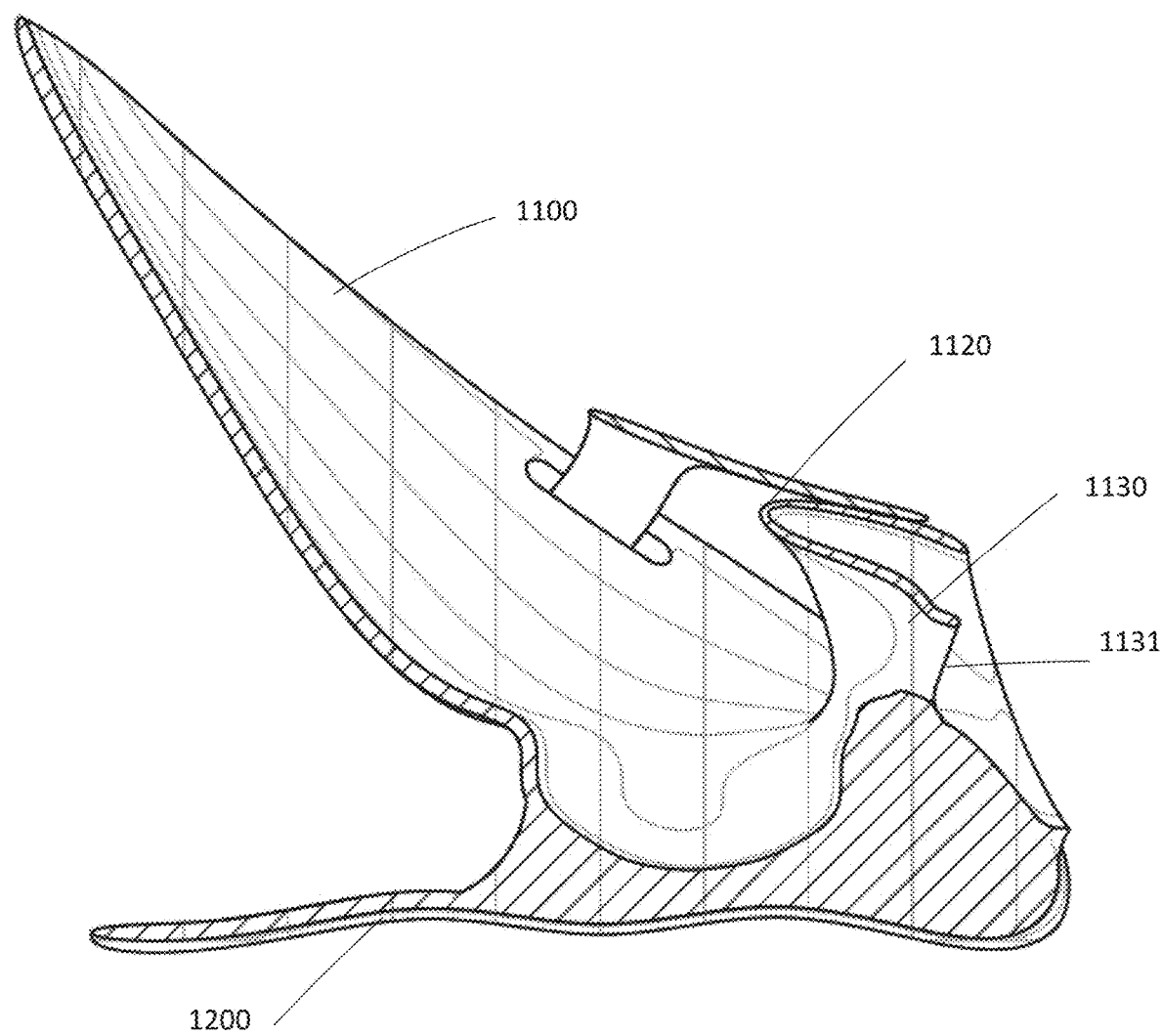
FIG. 3a is a cross-sectional side view taken along a centre-line passing along the length of the device of FIG. 3 and in which the curved backrest, hollow, saddle, and collection element are visible.
Figure 3B:
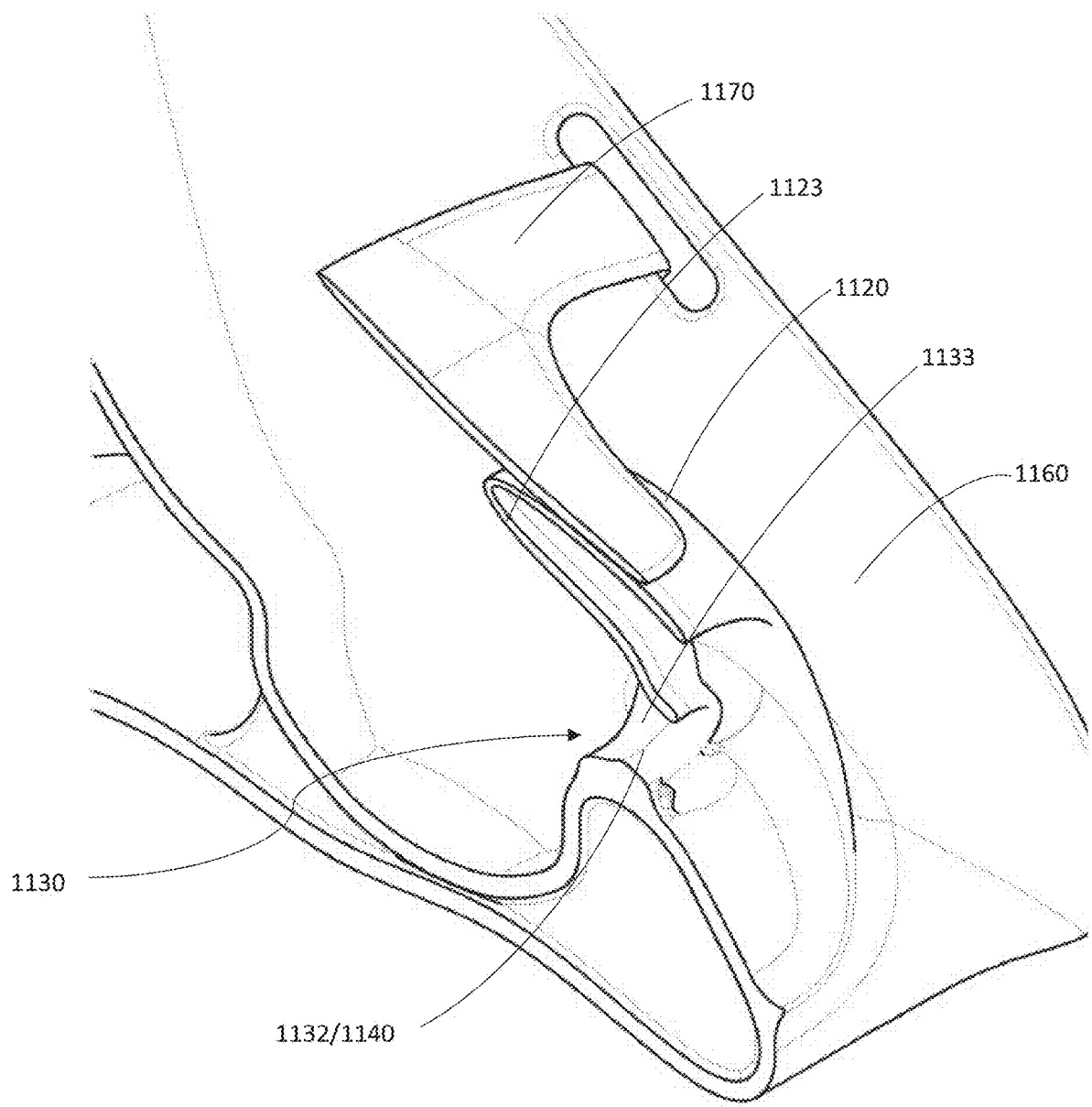
FIG. 3b is an isometric cut-away view of the device of FIG. 1 and in which the hollow, saddle and collection element are visible
Figure 4:
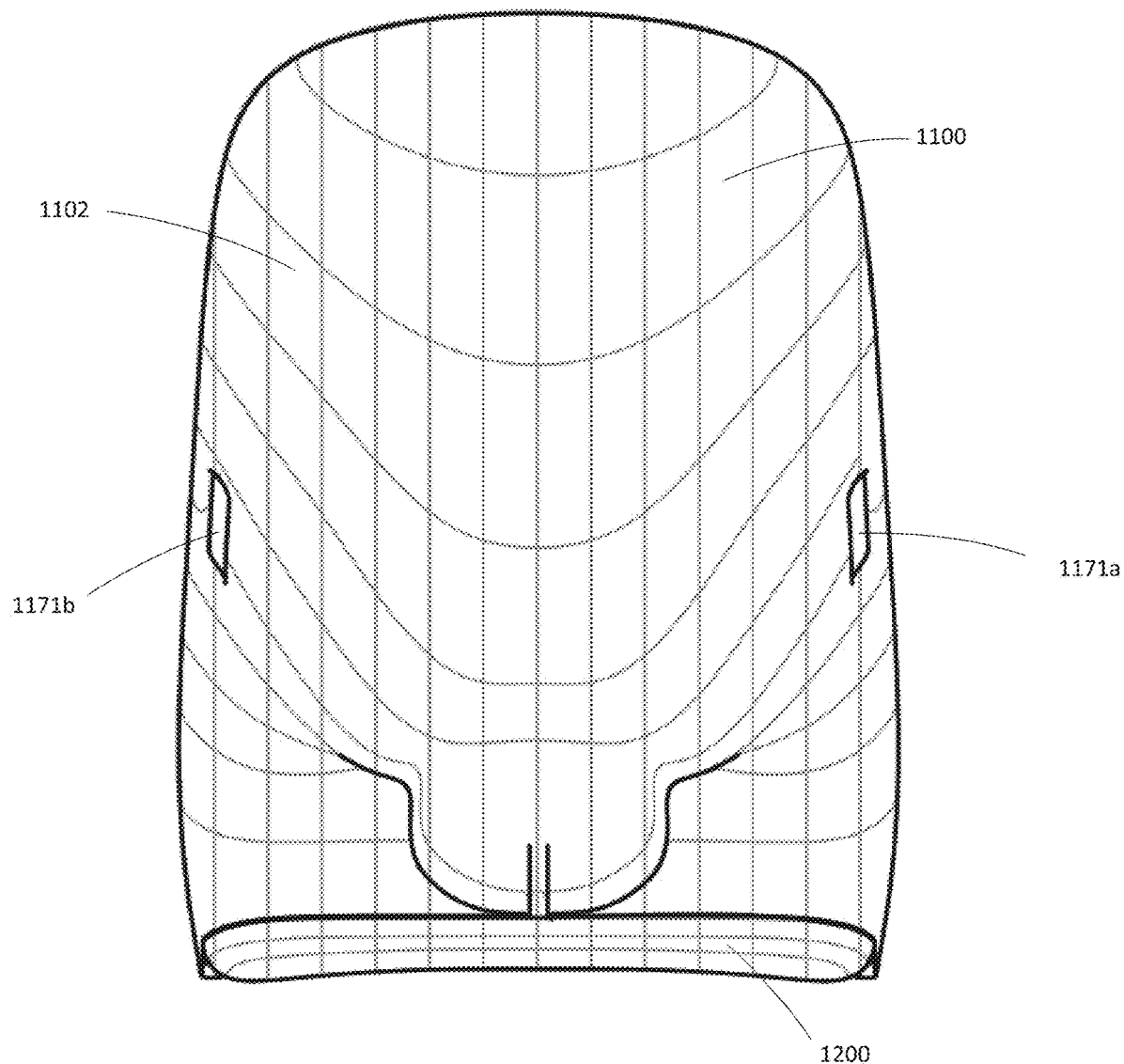
FIG. 4 is a rear view of the seat assembly of FIG. 1, in which ends of the retaining member can be seen extending through openings on each side of the backrest and attaching to the rear surface of the backrest.
Figure 11:
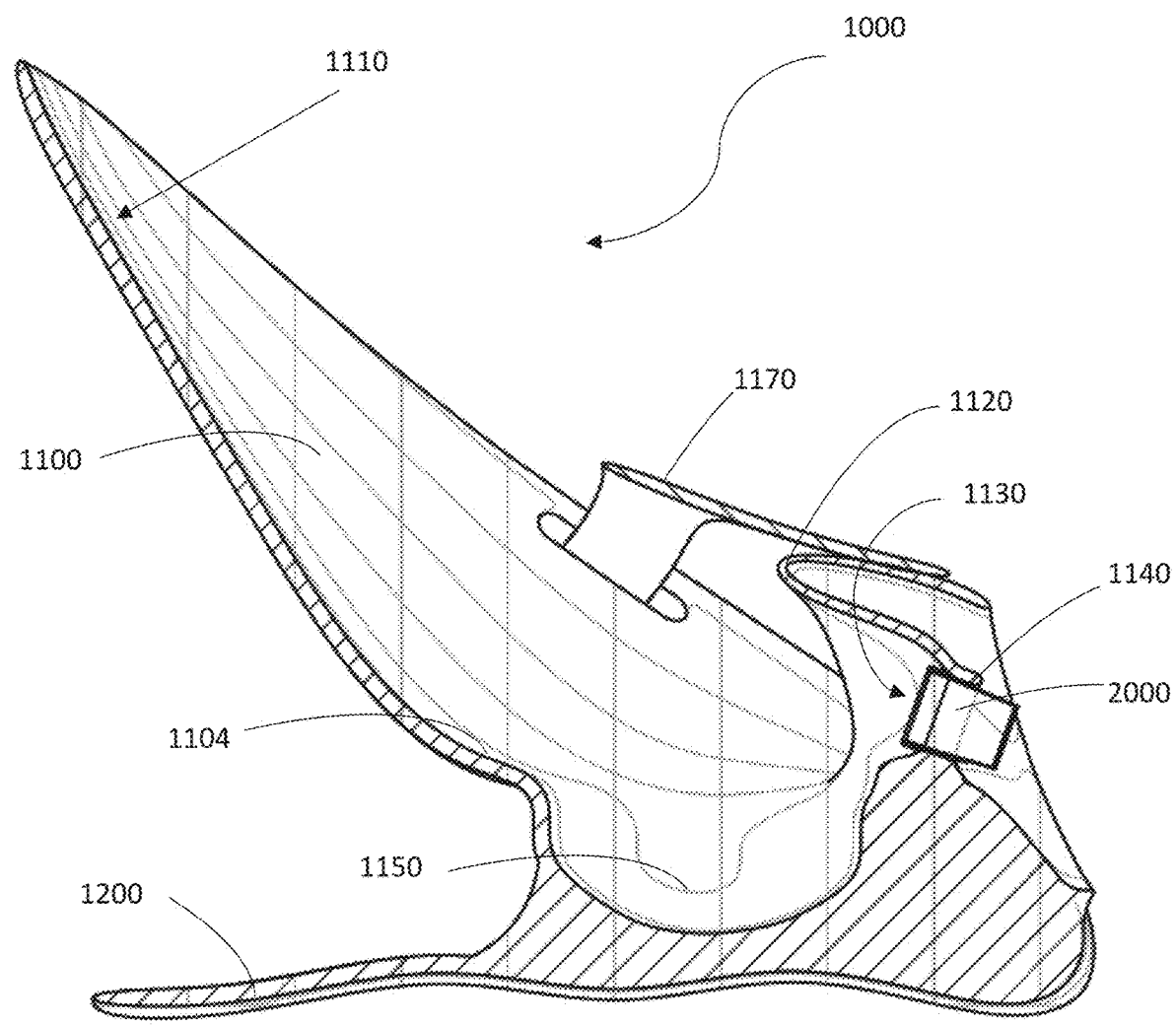
FIG. 11 is a cross-sectional side view of taken along a centre-line passing along the length of the device of FIG. 3 and in which the cup of FIG. 9 is mounted within the collection element.

The saddle 1120 at least partially surrounds a hollow interior in which the collection element 1130 is located. As shown in FIGS. 3a, 3b and 11, the saddle 1120, particularly an inner surface of the central portion of the saddle, forms a shield around the collection element 1130 to reduce the risk of urine spraying outside of the collection element. For example, interior walls 1123 of the saddle 1120, which may also form side walls 1133 of the collection element 1130, may block urine being sprayed into the clinical environment and onto people nearby.

Figure 9:
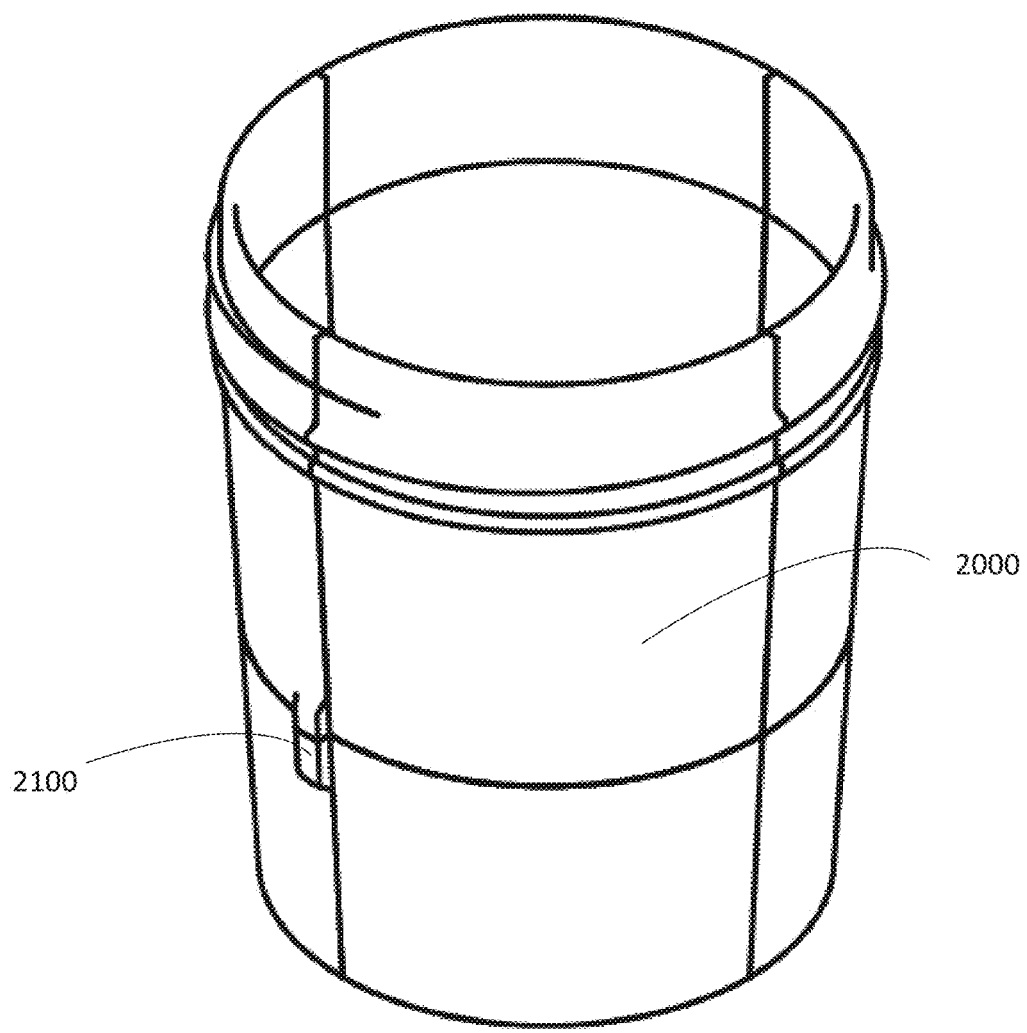
FIG. 9 is an isometric view of one form of cup to be used with the device of the present technology.
Figure 10:
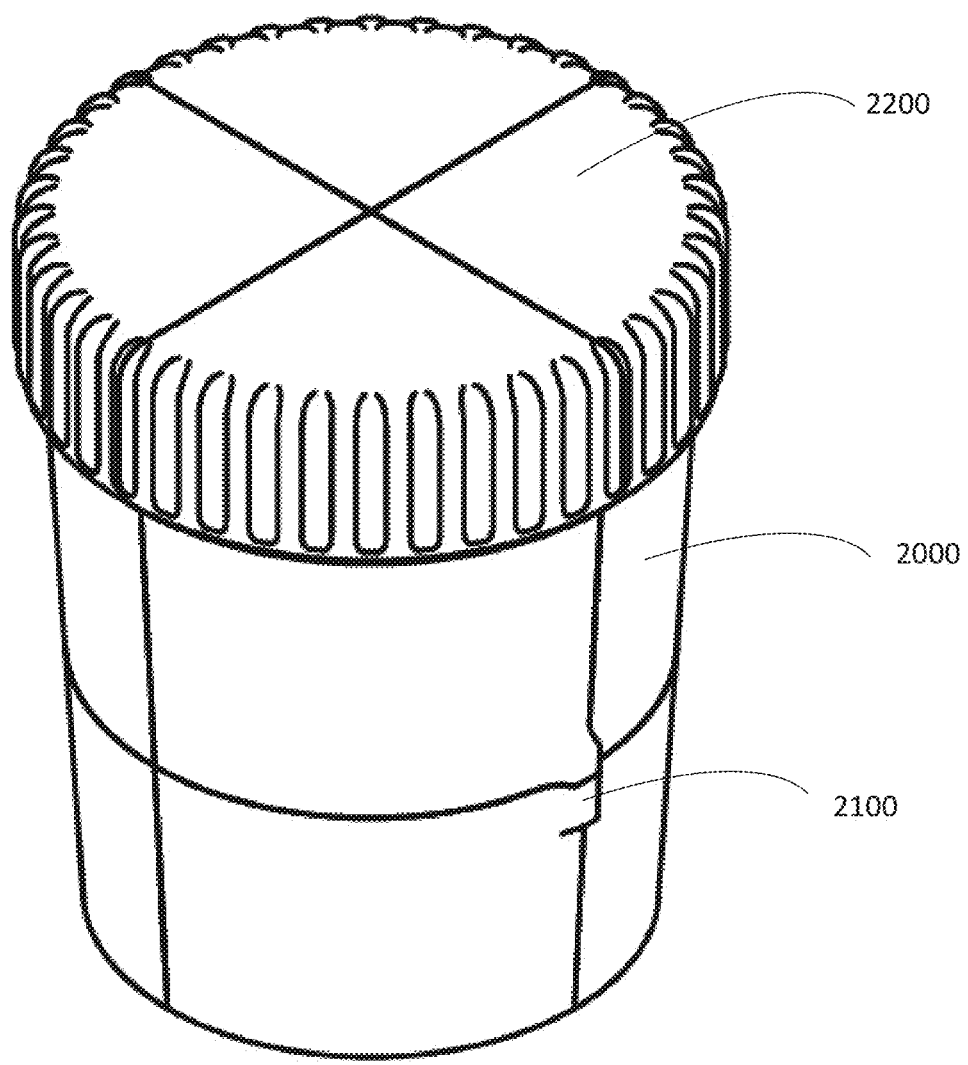
FIG. 10 is an isometric view of the cup of FIG. 9 and to which a lid is attached.

The collection element 1130 is located within the hollow interior of the saddle and is configured to receive a urine collection cup 2000 for holding collected urine. Typically, the cup 2000 is a single use cup that is removable and replaceable, but in some forms the cup may be capable of being removed, sterilized, and reused. In some forms, as shown in FIGS. 9 and 10, the cup 2000 comprises a removable lid 2200 for sealing a urine sample within the cup 2000. In other forms, the cup 2000 does not comprise a lid. The collection element 1130 may comprise a cup mount 1140 for locating the urine collection cup within the element 1130.

In some forms, as shown in FIG. 3b, the collection element 1130 comprises a cup receiving opening 1131 defined by a rim 1132. The cup receiving opening 1131 is shaped and dimensioned to receive at least a portion of a urine collection cup 2000. For example, the cup receiving opening may be substantially circular and may comprise a substantially annular rim to receive a collection cup having a substantially circular transverse periphery. Alternatively, the cup receiving opening may be substantially oblong and may comprise a substantially oblong rim to receive a collection cup having a substantially oblong transverse periphery. The transverse periphery is the periphery of side walls of the cup, transverse to the height of the cup. Therefore, the collection cup 2000 may comprise a varying diameter or width along the height of the cup, especially if the cup is tapered to be narrower at the bottom and wider at the top. The cup receiving opening 1131 typically has a diameter or width that is larger than the diameter or width of a lower portion of the cup and that is smaller than the diameter or width of an upper portion of the cup. In this configuration, the lower portion of the cup may be inserted through the cup receiving opening 1131 until the diameter or width of the cup 2000 substantially corresponds with the diameter or width of the opening 1131. At this point, an outer surface of the cup 2000 may contact the rim 1132 of the cup receiving opening 1131. For example, an outer side surface of the cup 2000 may press against an inner surface of the rim 1132 to suspend the cup within the cup receiving opening 1131. In effect, the rim 1132 engages with the urine collection cup 2000 to hold the cup within the collection element 1130. The wider upper portion of the cup 2000 extends above the opening 1131 and prevents the cup 2000 from moving further down into the opening 1131. In this way, the collection cup 2000 is suspended within the opening 1131 and the rim 1132 of the opening 1131 provides a mount 1140 for the cup 2000.

In other forms, the collection cup 2000 may be generally cylindrical and may comprise an outwardly projecting flange at its rim. The flange may comprise a diameter larger than the diameter of the cup receiving opening 1131 and therefore the cup 2000 is inserted through the cup receiving opening 1131 from above until the flange abuts the rim 1132 of the opening. In this position, the cup is suspended within the opening and the rim 1132 provides a mount 1140 for the cup. Again, the rim 1132 engages with the urine collection cup 2000 to hold the cup within the collection element 1130. In this form, the flange may be sufficiently thick to prevent contaminated urine running into the collection cup 2000 after contacting a surface of the collection element 1130 and running down the surface of the element 1130 and into the cup 2000.

In other forms, the cup mount 1140 may comprise one or more projections extending into the cup receiving opening 1131 and the collection cup 2000 may be supported by or mounted on the one or more projections.

In other alternative forms, the collection element 1130 may comprise a bottom surface on which a collection cup 2000 sits. In this arrangement, the bottom surface forms a cup mount 1140 for the collection cup and supports the collection cup within the collection element. In preferred forms, the bottom surface comprises one or more openings, such as holes or perforations, to allow urine overflow and any other fluids to exit the collection element.

Optionally, a secondary collection device, such as an absorbent material or a containing item, may be located beneath the opening(s) in the collection element 1130 to collect any spilled urine or fecal overflow. For example, a towel, container, fluid impermeable bag, bowl or the like may be utilized.

In some forms, the collection element 1130 comprises one or more side walls 1133 configured to direct urine toward the cup receiving opening 1131. For example, the one or more side walls 1133 may slope toward the opening 1131, as shown in FIGS. 3b and 11. In some forms, the collection element 1130 is generally annular and comprises a single curved or circular side wall that slopes toward the cup receiving opening 1131 in a generally conical or frustoconical configuration. In other forms, the collection element 1130 may of any other suitable shape, whether regular or irregular in shape, and may comprise multiple side walls that slope toward the cup receiving opening 1131. The sloping side walls 1133 encourage any urine spilled within the element 1130 to flow toward the cup receiving opening 1131 so as to be released through the opening 1131 once the cup 2000 is removed.

Because it is important that uncontaminated urine is received within the collection cup 2000, it is important to position the patient correctly on the device/chair 1000. The saddle 1120 and the backrest 1110 help to position the patient correctly. For example, a female patient will typically be placed in a reclined position, leaning against the backrest 1110 with one leg on either side of the saddle to encourage her urine flow to raise upwards and into the collection cup 2000. A male patient will typically be placed in more of an upright position with on leg on either side of the saddle and he may hold onto an upper surface of the saddle 1120 to retain that upright position. In this position, a flying stream of his urine flow is more likely to be received within the collection cup 2000 without being contaminated by contacting the collection element 1130 or other parts of his body.

To further help position the patient to catch a flying stream of uncontaminated urine flow, the seat portion 1100 of the device 1000 may comprise a hollow 1150 to receive at least a portion of a patient's buttocks therein. The hollow 1150 may be located between the backrest 1110 and the saddle 1120. The hollow 1150 may comprise a bottom surface 1151 that may slope rearwardly, may be substantially horizontal, concave, or may slope forwardly towards the saddle opening 1124 and the collection element 1130.

In some forms, the backrest 1110 comprises a lumbar support 1115, located above the hollow 1150, for additional patient comfort.

The backrest 1110 typically extends from the hollow 1150, or from a shelf region 1104 proximate the hollow, to a rear edge 1111 of the backrest. The rear edge of the backrest may also form the rear edge of the seat portion 1100. The backrest 1110 may also comprise first and second sides that form at least a portion of the first and second sides 1103a, 1103b of the seat portion 1100.

Figure 8:
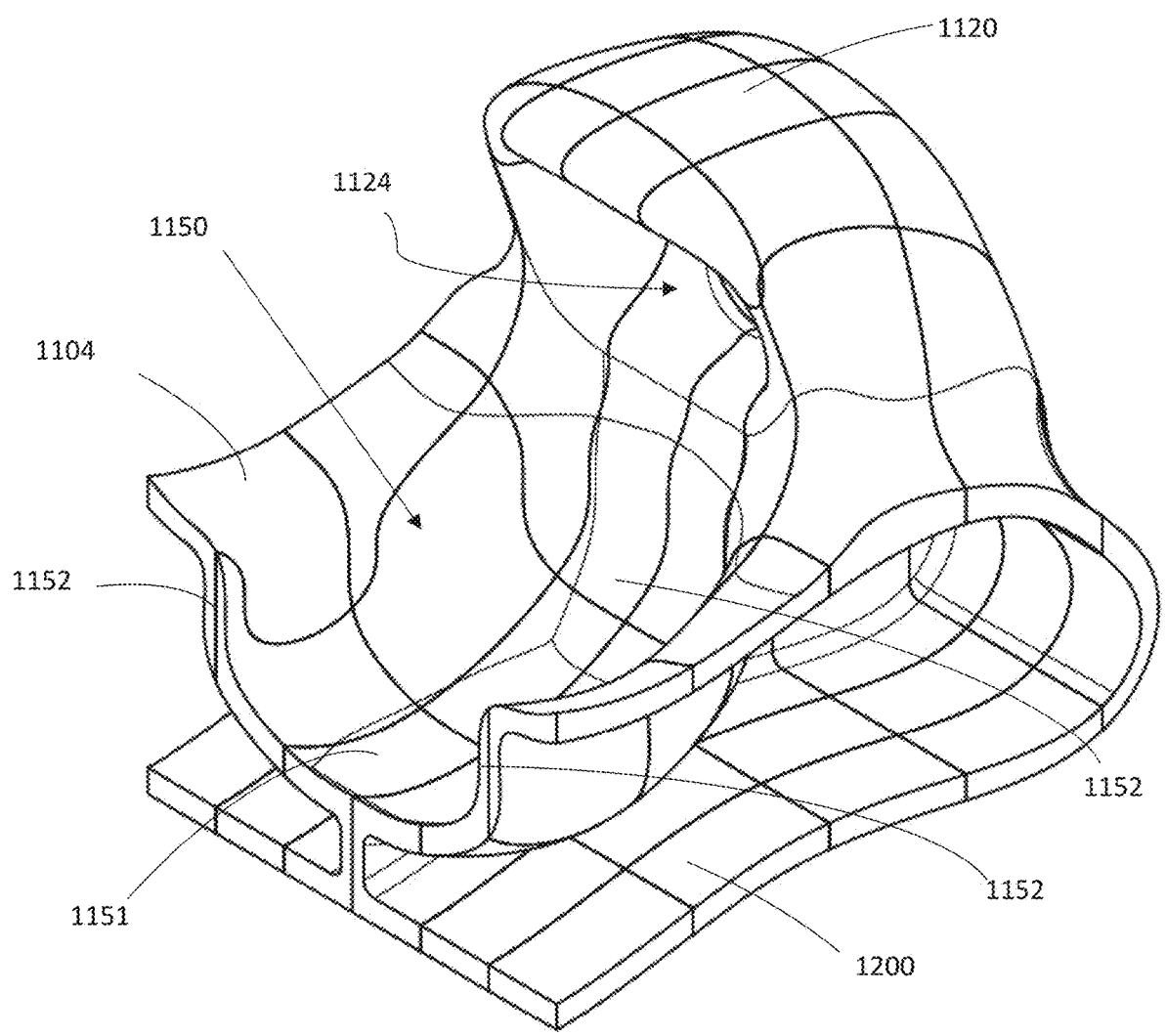
FIG. 8 is an enlarged isometric cut-away view showing a portion of the device of FIG. 5 and in which the hollow, saddle and collection element are visible.

In some forms, as shown in FIG. 8, the hollow 1150 is at least partially defined by one or more side walls 1152. For example, a single curved side wall may surround the hollow or multiple side walls may fully or partially surround the hollow 1150. In some forms, a shallow side wall 1152 is provided between the hollow 1150 and the collection element 1130 to discourage fecal matter from entering the collection element. This arrangement is particularly useful where the bottom surface 1151 of the hollow is horizontal or slopes toward the collection element 1130, although the arrangement may also be used whether the bottom surface of the hollow slopes rearwardly. In other forms, a front portion of the hollow 1150 may meet a sloping wall of the collection element 1130, preferably at a gentle curve, for greater patient comfort. This arrangement is often, but not exclusively, used with a hollow that has a bottom surface that slopes rearwardly, away from the collection element.

In other forms, as shown in FIG. 11, the seat portion 1100 comprises a hollow 1150 that is at least partially defined by a shelf region 1104 that surrounds at least a portion of the hollow and that preferably curves around at least a rear portion and side portions of the hollow 1150. In some forms, the shelf region 1104 may fully surround the hollow 1150. The shelf region 1104 is configured to allow at least a portion of the patient's buttocks to rest on the shelf region 1104, with the patient's anus located above the hollow 1150. The shelf region 1104 may be generally curved and ergonomically shaped for comfort. In this form, the hollow 1150 comprises one or more side walls 1152 that extend between the bottom surface 1151 of the hollow and the shelf region 1104 so that the hollow 1150 forms a cavity for containing waste, such as fecal material and spilled urine. The shelf region 1104 allows the patient to sit above the hollow 1150, away from contact with the waste. After the patient has been removed from the device/chair, the waste may be poured out from the hollow 1150 and the entire device/chair, including the hollow, may be thoroughly cleaned before further use.

In some forms, the backrest 1110 comprises a central portion located between two side portions. Each of the side portions terminate at respective left and right sides 1103a, 1103b of the seat portion 1100. In some forms, as shown in FIGS. 1, 2, 5, 6, 16 and 18, the backrest 1110 is angled or curved between the left and right sides 1103a, 1103b to form a substantially trough-like profile, in which the central portion of the backrest is rearward of the left and right sides 1103a, 1103b.

In some forms, as shown in FIGS. 1 and 5, the seat portion 1100 also comprises a pair of leg wells 1160 to receive a patient's legs therein. Each of the leg wells 1160 extends along the seat portion 1100 on either side of the saddle 1120. For example, one of the pair of leg wells extends between a respective one of the pair of outer side walls of the saddle frame and a respective one of the left and right sides of the seat portion. Each leg well 1160 may be ergonomically formed for comfort. For example, each leg well 1160 may comprise a curved channel, generally shaped and dimensioned to receive the curved portion at the rear of the patient's legs, especially the thighs and calves.

In some forms, as shown in FIGS. 1 to 4, 11, 17 and 18, the device/chair 1000 may also comprise a retaining member 1170 that spans across the seat portion 1100, between the left and right sides 1103a, 1103b of the seat portion. The retaining member 1170 is attachable to the seat to prevent a patient from falling off or moving off the device 1000. In some forms, the retaining member 1170 is at least partially or fully detachable from the seat, and preferably to the seat portion 1100, so that the retaining member 1170 can be partially or fully removed in order to position a patient on the device 1000 or to remove a patient from the device 1000. In other forms, the retaining member 1170 is fixed to the device 1000 and the patient is slid between the retaining member and the seat portion 1100 by sliding the body of the patient along the backrest 1110 toward the saddle 1120 and between the retaining member 1170 and seat portion 1100. This configuration may be useful where the patient is a small child, but it is generally too difficult for larger patients, especially adults.

In some forms, the retaining member 1170 may comprise a strap that extends substantially horizontally from left to right across the seat portion 1100 of the device/chair 1000 and attaches to each side 1103s, 1103b of the seat portion 1100. The strap is typically positioned to extend across a patient's lower ribs or belly region. In other forms, the retaining member 1170 may comprise a strap or sash that extends substantially diagonally from left to right across the seat portion of the device/chair and that attaches to each side of the seat portion 1100. The strap/sash is typically positioned to extend across one shoulder of the patient and toward the opposite hip or lower rib cage.

Figure 12:
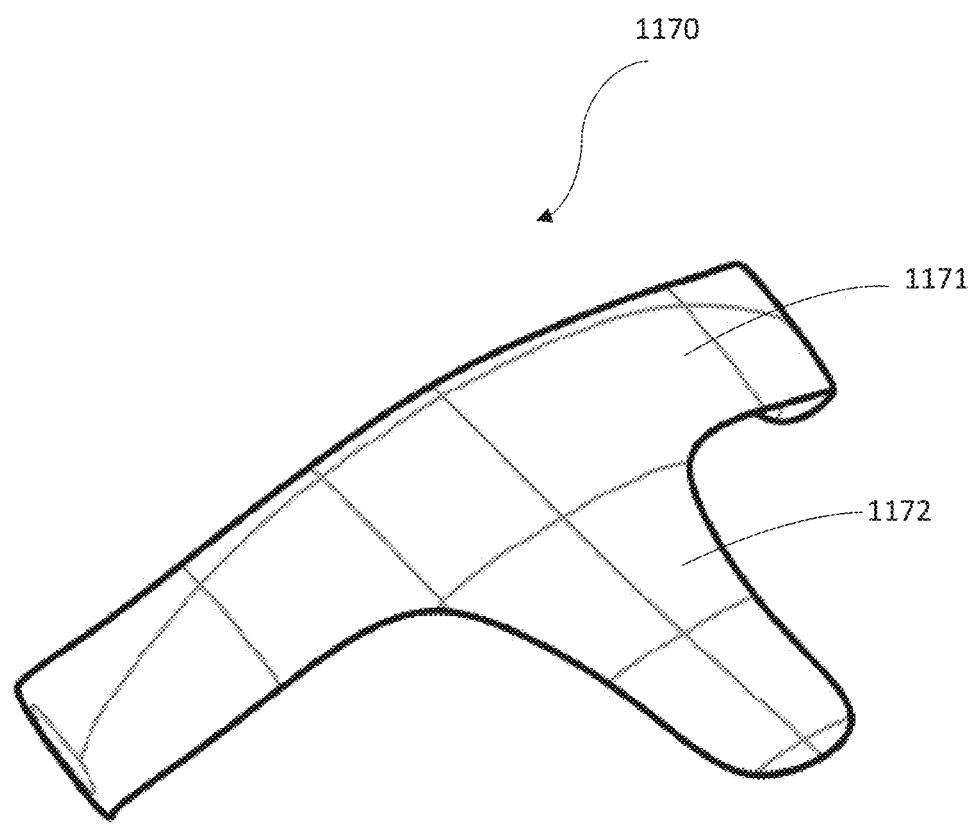
FIG. 12 is an isometric front view of one form of retaining member that may be used with the device of the present technology.
Figure 13:
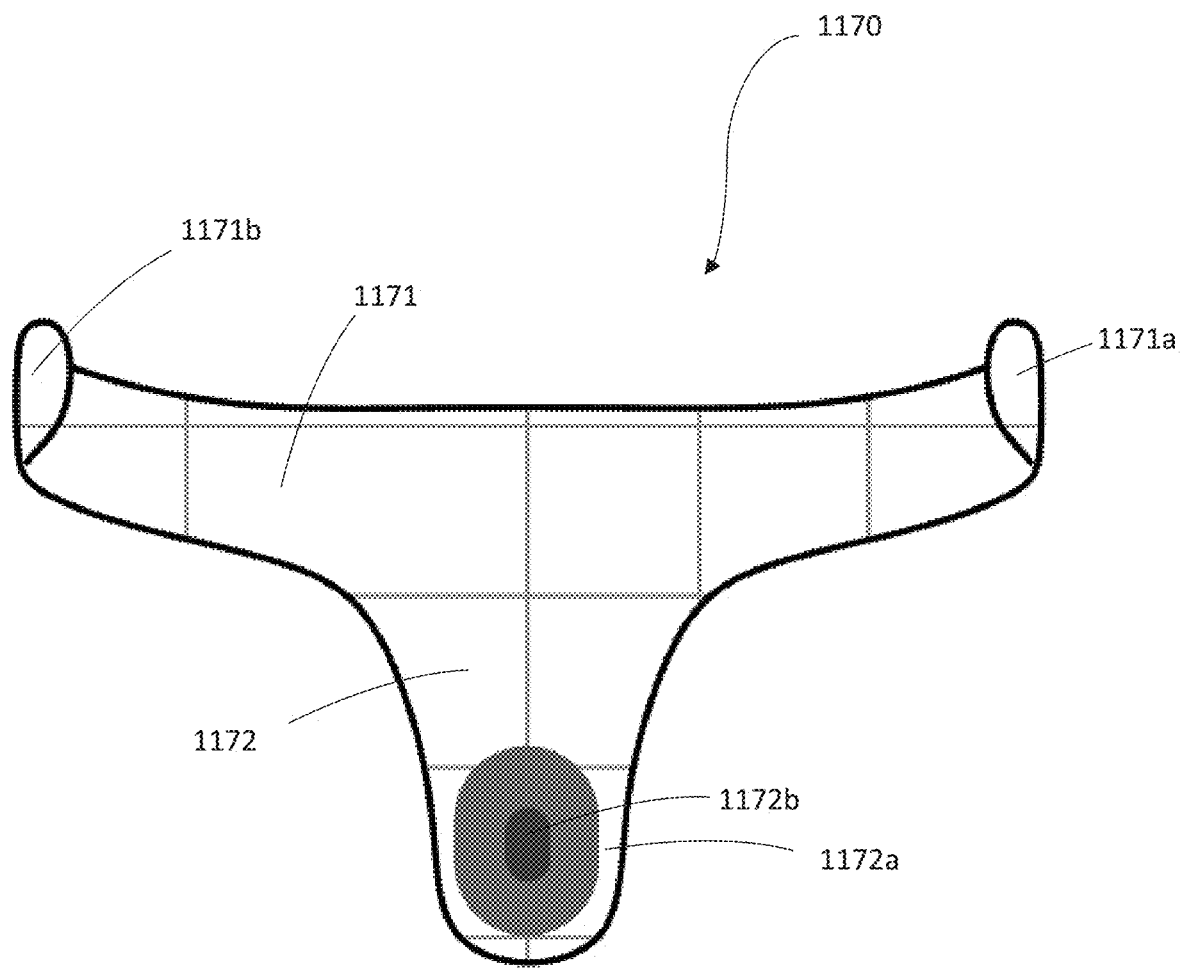
FIG. 13 is an isometric rear view of the retaining member of FIG. 13.
Figure 14:
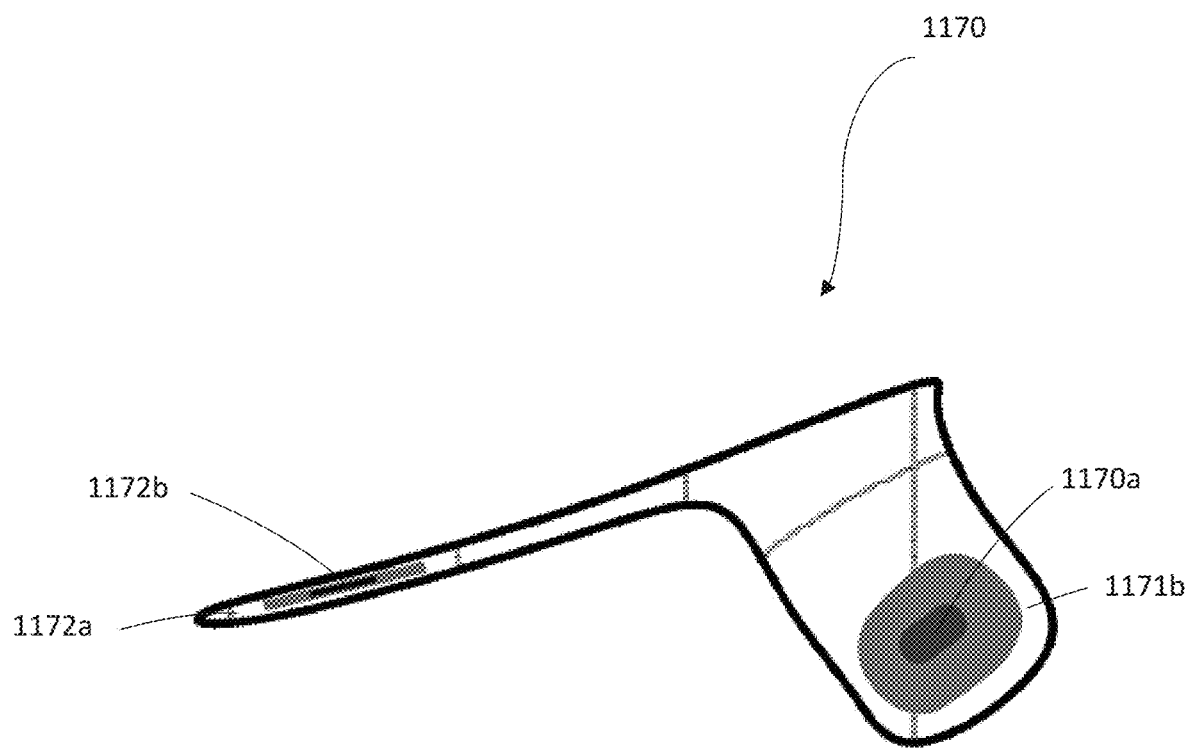
FIG. 14 is a side view of the retaining member of FIG. 13.

In yet other forms, as shown in FIGS. 12 to 14, the retaining member 1170 comprises a substantially T-shaped three-point harness, which may comprise a first strap 1171, that extends substantially horizontally from left to right across the seat portion 1100 of the device/chair 1000, and a second strap 1172, that extends substantially vertically from a central region of the first strap 1171 to the saddle 1120. In some forms, the harness 1170 is positioned so that the first strap 1171 spans across the patient's rib cage or belly region and between the left and right sides 1103a, 1103b of the seat portion 1100. In other forms, the harness 1170 may be positioned so that that the first strap 1171 spans across the patient's chest, such that the first strap 1171 extends under the arms of the patient or across the upper arms of the patient. The position of the harness 1170 will, to some extent, depend on the size of the patient.

In some forms, the retaining member 1170 may be adjustable to adjust its position to suit the patient and/or to adjust its size to suit the patient. For example, the strap of the retaining member may have an adjustable length. Where the retaining member 1170 is a three-point harness, the first strap 1171 and/or the second strap 1172 may be adjustable in length so as to make the harness 1170 smaller or larger.

In some forms, as shown in FIGS. 12 to 14, the first strap 1171 comprises a first end 1171a that attaches to one side of the backrest, such as the left side 1103a, and a second end 1171b that attaches to the other side of the backrest 1110, such as the right side 1103b. The second strap 1172 comprises a third end 1172a that attaches to the saddle 1120. In some forms, the third end 1172a attaches to a top surface of the central portion 1121 of the saddle.

In some forms, the seat portion comprises at least one engagement feature 1105 for engaging with the retaining member 1170 to attach the retaining member to the seat portion. Typically, the retaining member 1170 comprises first and second ends for attaching to a respective engagement feature of the seat portion 1100. Where the retaining member 1170 comprises a three-point harness, the at least one engagement feature 1105 of the seat portion engages with a respective one of the first and second ends 1171a, 1171b of the first strap 1171. Typically, engagement features are located on each side 1103a, 1103b of the seat portion 1100.

In some forms, at least one of the ends of the retaining member 1170 comprises one or more hooks, loops, magnetic regions or other suitable features to engage with at least one engagement feature 1105 provided on the seat portion in order to detachably attach the retaining member to the seat portion. The engagement feature 1105 may be any suitable feature for engaging with the retaining member 1170. For example, the engagement feature may comprise hook or loop fasteners for engaging with complimentary loop or hook fasteners provided on the ends of the retaining member, such as on the first and second ends of the first strap of a three-point harness. In other forms, the engagement feature may comprise a hook for engaging with a complimentary hook or loop provided on ends of the retaining member, such as on the first and second ends of the first strap of a three-point harness. In other forms, the engagement feature may comprise a recess for engaging with a complimentary hook provided on the ends of the retaining member, such as on the first and second ends of the first strap of a three-point harness. In yet other forms, the engagement feature 1105 may comprise an opening, such as a slot, hole for engaging with a complimentary hook provided on the ends of the retaining member, such as on the first and second ends 1171a, 1171b of the first strap of a three-point harness. Alternatively, the respective end of the retaining member 1170 or first strap 1171 may be inserted and then wrapped back on itself to attach to another region of the retaining member 1170 or first strap 1171, such as by a dome, snap attachment, button, hook and loop fasteners, or by any other suitable form of attachment. In some forms, the engagement feature 1105 may comprise a combination of components for engaging with the retaining member 1170.

In some forms, as shown in FIGS. 15 to 18, the retaining member 1170 detachably attaches to an engagement feature 1105 of the seat portion 1100 by a magnetic connection. In these forms, at least one of the first and second ends of the retaining member 1170 comprises a magnetic region, comprising one or more magnets or a suitable metal for attracting a magnet of the engagement feature 1105 of the seat portion 1100. The engagement feature 1105 may be provided on or accessible from the rear surface 1102 of the seat portion 1100 and comprises at least one magnetic region to which the ends of the retaining member 1170 may be attached. The magnetic region of the engagement feature 1105 may comprise one or more magnets or a suitable metal for attracting a magnet of the retaining member.

Figure 15:
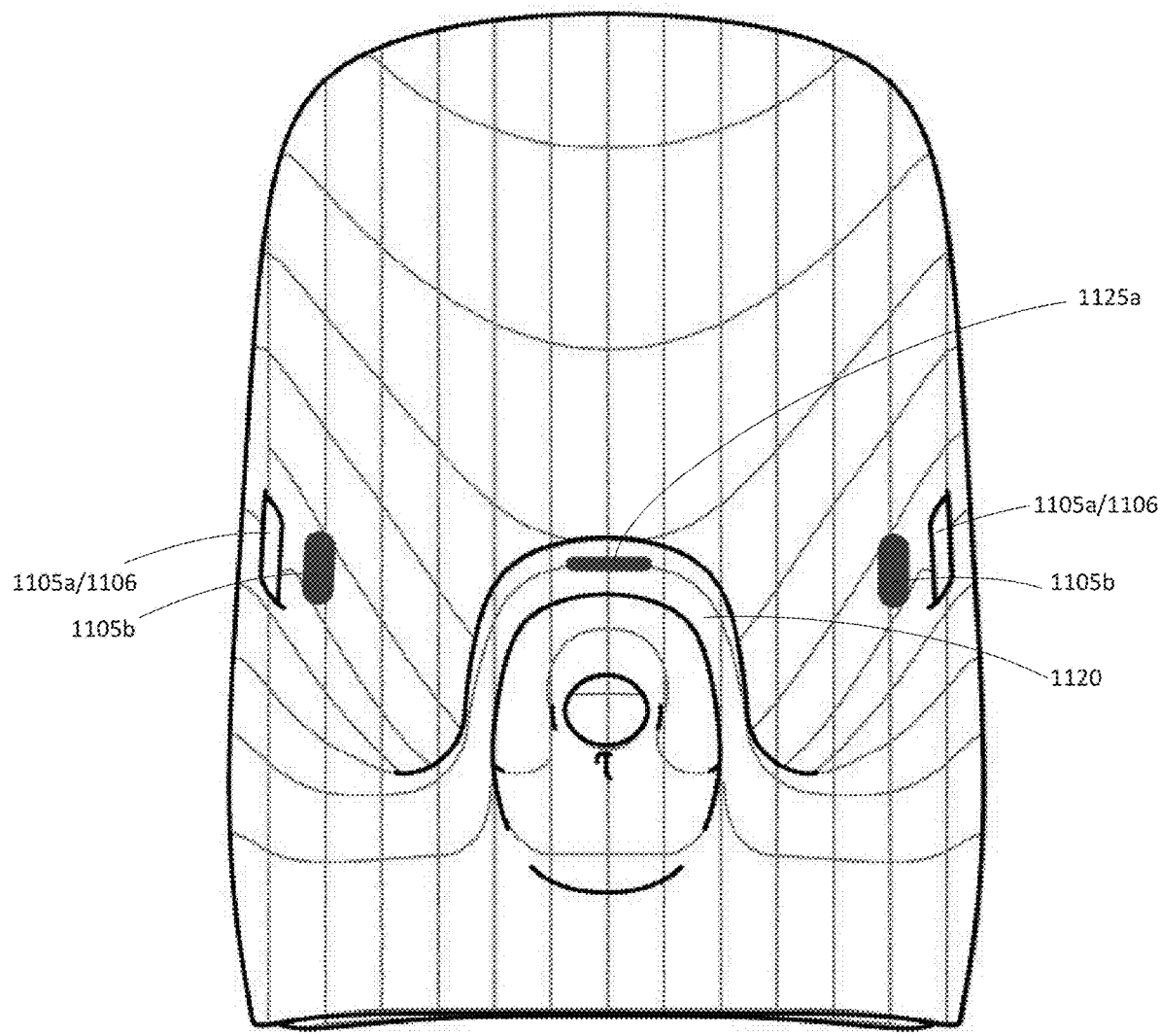
FIG. 15 is a front view of one form of device according to the present technology in which the seat portion comprises engagement features comprising openings at the sides of the backrest and magnetic regions comprising magnets embedded in the backrest and the upper surface of the saddle.
Figure 16:
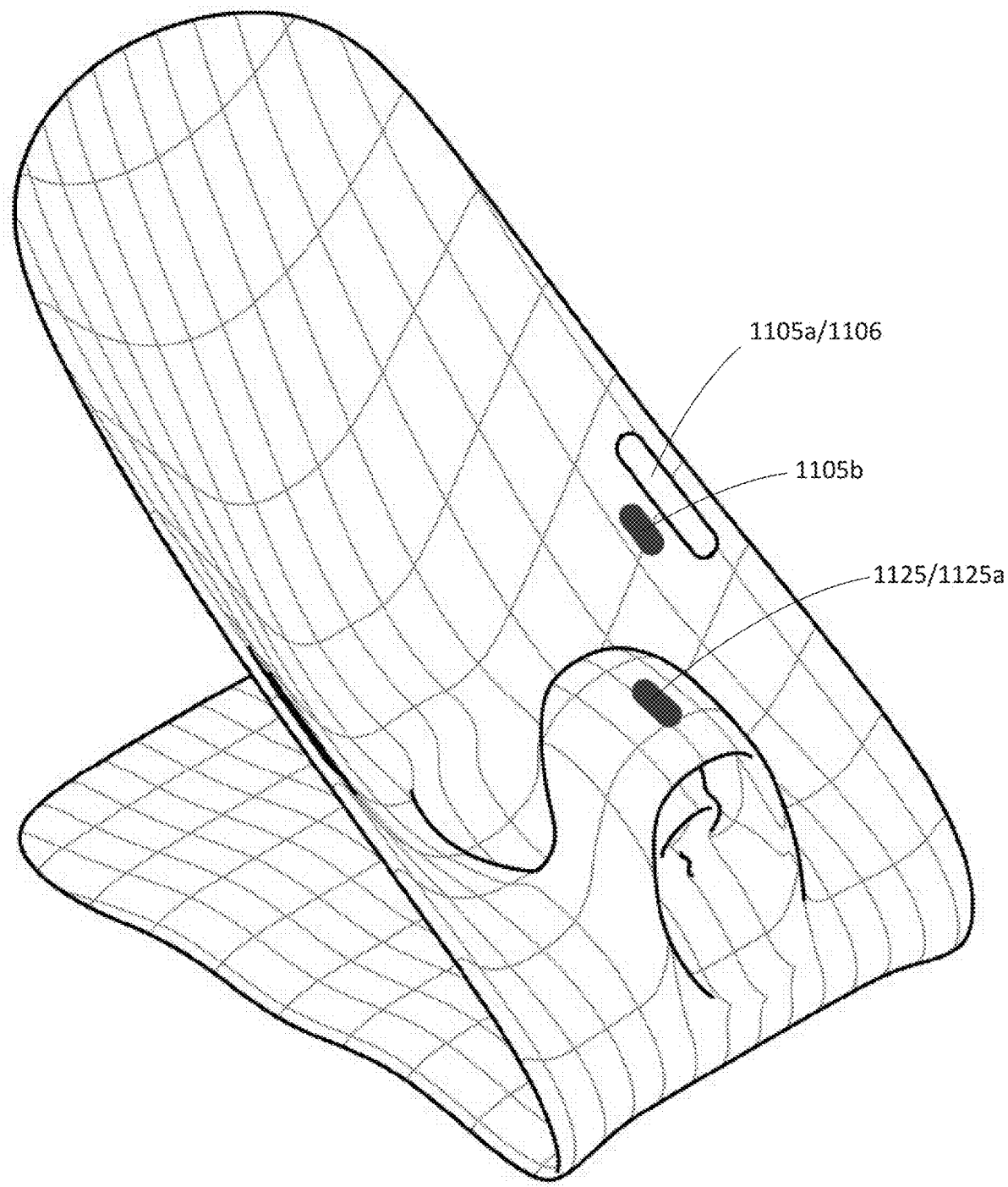
FIG. 16 is an isometric view of the device of FIG. 16.

Returning to the embodiment shown in FIGS. 15 and 16, where the retaining member 1170 comprises a three-point harness, as shown in FIGS. 12 to 14, each engagement feature 1105 of the seat portion may comprise a magnetic region 1105b for engaging with a complimentary magnetic region provided on the first and second ends 1171a, 1171b of the first strap. For example, a magnetic region comprising one or more magnets may be provided on one or each of the first and second ends of the first strap 1171a, 1171b. The magnetic region of the engagement feature 1105b may also comprise one or more magnets or may comprise a metal for attracting the magnet(s) of the first strap 1171. Conversely, the magnetic region of the engagement feature 1105 may comprise one or more magnets for attracting a suitable metal provided on the respective end of the first strap 1171.

In some forms, as shown in FIGS. 15 and 16, the engagement feature 1105 comprises both an opening 1105a, such as a slot or hole, on either side of the seat portion 1100 and a magnetic region 1105b on the rear surface 1102 of the seat portion, proximate the opening 1105a. The magnetic region 1105b may comprise one or more magnets or a suitable metal, for engaging with a complimentary magnetic region 1170a provided on the retaining member 1170. In this form, at least one end of the retaining member 1170 or the first strap 1171 comprises a magnetic region 1170a, as described above, for engaging with the magnetic region 1105b of the seat portion 1100. In this arrangement, one end of the retaining member 1170 or first strap 1171 is insertable through the respective opening 1105a from the front of the seat portion 1100 and is then folded or bent against the rear of the seat portion so that the magnetic regions 1105b and 1170a contact each other to attach the retaining member 1170 or strap 1171 to the seat portion. Where each end of the retaining member 1170 is detachably attachable to the seat portion, each of the first and second ends of the retaining member is insertable through a respective opening 1105a in a respective side of the seat portion and is detachably attachable to the magnetic region on the rear surface 1102 of the seat portion 1100. Alternatively, one end of the retaining member may be fixed to the seat portion 1100.

In some forms, the openings 1105a in the seat portion may have a dual purpose and may be used to receive an end of the retaining member 1170 and used as handles 1106 to lift and relocate the device/chair 1000, as shown in FIGS. 5 and 6.

In some forms, as shown in FIGS. 15 and 16, the magnetic region 1105b of the seat portion 1100 comprises one or more magnets that are embedded within the seat portion or that are covered or over-moulded with a polymer to avoid creating bacterial traps.

Where the retaining member 1170 comprises a three-point harness, the third end 1172a of the retaining member may be fixedly attached to the saddle 1120 by any suitable form of attachment, such as by moulding, adhering, welding. Alternatively, the third end 1172a may be detachably attached to the saddle by a saddle engagement feature 1125. In some forms, the saddle engagement feature may comprise hook or loop fasteners for engaging with corresponding loop or hook fasteners of the third end 1172a of the harness. In other forms, the saddle engagement feature may comprise a hook, opening, or recess for engaging with a complimentary hook of the third end 1172a. In yet other forms, the saddle engagement feature may comprise a hook for engaging with a loop of the third end 1172a. In preferred forms, the retaining member 1170 is detachably attachable to the saddle via a magnetic connection. In these forms, as shown in FIGS. 15 and 16, the saddle engagement feature 1125 comprises a magnetic region 1125a and the third end 1172a of the retaining member 1170 also comprises a magnetic region 1172b that attaches to the saddle when the magnetic regions are placed in contact. The magnetic regions 1125a, 1172b may comprise one or more magnets. In some forms, a first one of the magnetic regions 1125a, 1172b may comprise one or more magnets and the other of the magnetic regions 1125a, 1172b may comprise a suitable metal that attracts the one or more magnets of the first magnetic region 1125a, 1172b. In some forms, the saddle magnetic region 1125a is located on an upper surface of the saddle, such as on the upper surface of the central portion of the saddle 1120.

In some forms, as shown in FIGS. 15 and 16, the magnetic region 1125a of the saddle 1120 comprises one or more magnets that are embedded within the saddle or that are covered or over-moulded with a polymer to avoid creating bacterial traps.

In other forms, the retaining member 1170 may be attached to the base 1200 of the device using any of the methods and arrangements described above.

The retaining member 1170 may be made from any suitable material, but in preferred forms, the retaining member comprises a washable and reusable material, such as a polymer. In some forms, the retaining member comprises silicone and the one or more magnets are located within the silicone, so as to be located beneath an outer silicone surface of the retaining member, to provide the retaining member 1170 with a substantially smooth surface in order to avoid creating bacterial traps.

To assist with safety measures, the seat base 1200 optionally comprises a non-slip lower surface 1202. The non-slip lower surface may be textured or tacky.

In some forms, as shown in FIGS. 3, 7, 16 and 18 for example, the lower surface 1202 of the seat base comprises a pair of spaced apart, arcuate channels 1203 that extend from a left side of the seat base 1200 to a right side of the seat base to comfortably position the seat base on the thighs of an adult when the device is in use. The shape and dimensions of the channel may be selected to be ergonomically contoured to the shape and dimensions of the thighs of an average adult in order to maximise comfort.

The seat portion 1100 and seat base 1200 may be formed of any suitable material or combination of materials but are preferably selected from materials that are washable and reusable. In some forms, the material is capable of being sterilized prior to re-use. Typically, the seat portion and seat base comprise a polymer, such as polycarbonate.

To use the device of FIGS. 1 to 19, a sterile sample collection cup 2000 is located within the collection element 1130. A patient is placed on the seat portion 1100 such that the saddle 1120 is located between the patient's legs, the saddle opening 1124 is located in front of the patient's genitals and the backrest 1110 is behind the patient's back. The patient's posterior is at least partially located within the hollow 1150 or is resting on a shelf region 1104 proximate the hollow. The patient's legs extend along each side of the saddle 1120, preferably within leg wells 1160. If the patient is female, she will typically be encouraged to recline against the backrest 1110. If the patient is male, he will typically be encouraged to sit in a more upright position and may need to be held in this position by someone else. The patient may be positioned on the seat portion 1100 before or after the collection cup 2000 is located within the collection element 1130. The patient is preferably then held in place by attaching the retaining member 1170 to the seat portion 1100 (or base 1200).

Figure 17:
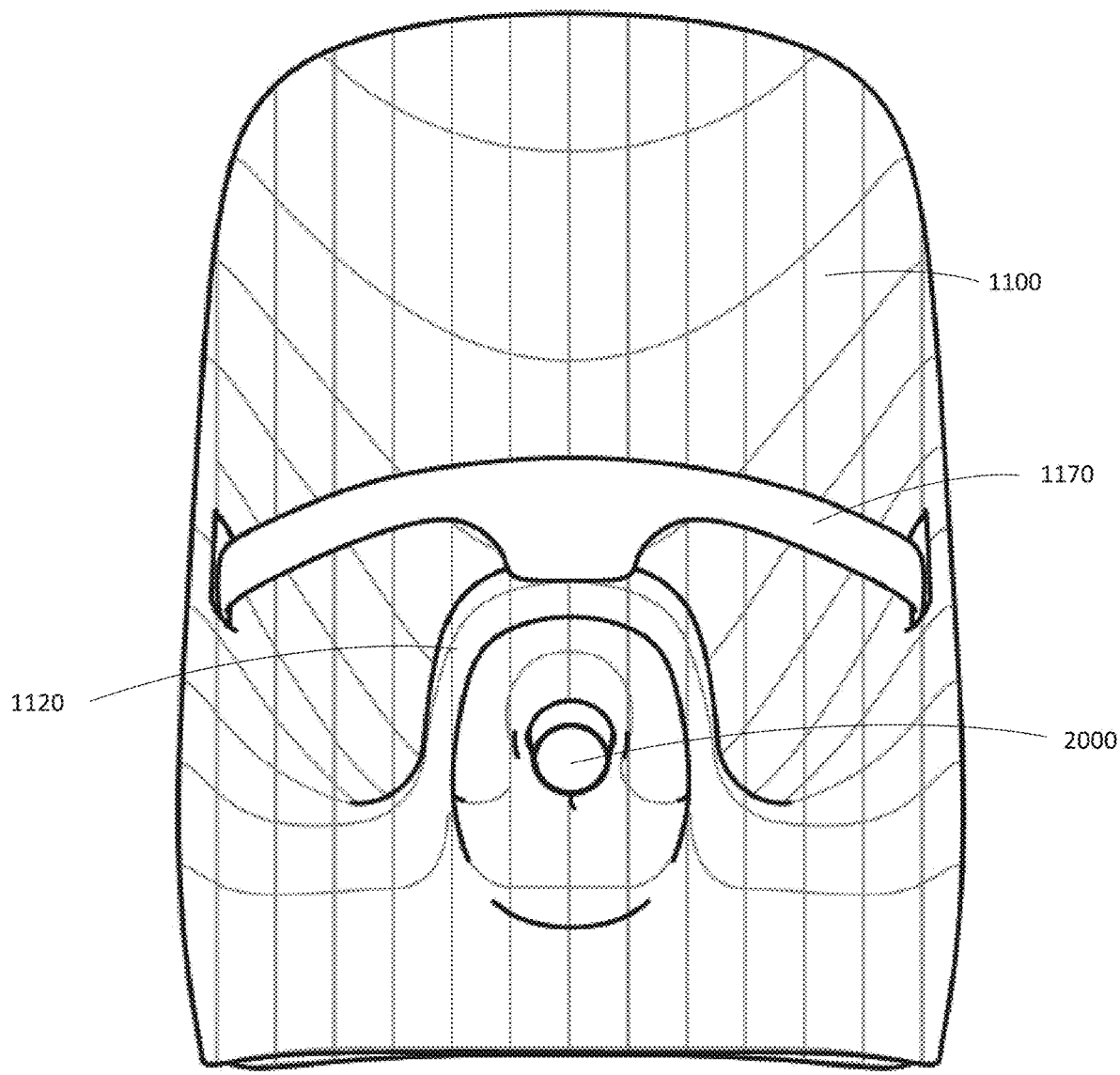
FIG. 17 is a front view of the device of FIG. 16 and in which one form of retaining member is attached to the seat.
Figure 18:
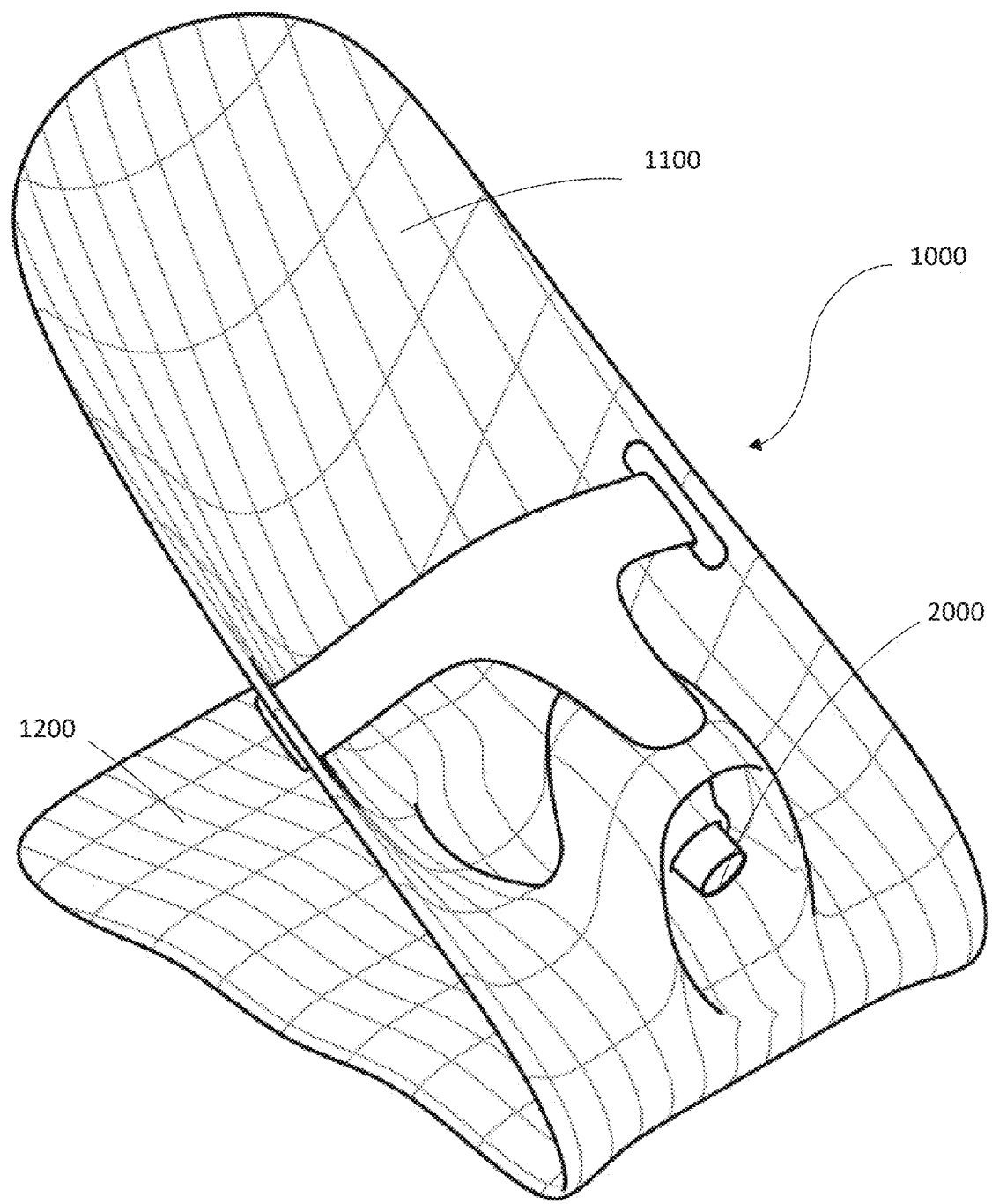
FIG. 18 is an isometric view of the device of FIG. 18 and in which a cup is mounted within the collection element.

The patient may be encouraged to urinate using known methods, such as rubbing the lower region of the patient's abdomen with a wet cotton bud. The reclined position of the seat portion 1100 allows a clinician to easily access the lower abdomen of the patient. When the patient urinates, the flying stream of urine is naturally directed into the collection element 1130 and into the collection cup 2000 within the element 1130. Where a clear sample cup is used, the device 1000 allows a clinician to easily see whether a urine sample has been collected in the cup 2000 by looking at the exposed lower portion of the cup 2000, as shown in FIGS. 17 and 18. Any fecal matter and urine overflow may be captured in the hollow 1150 or beneath the collection element 1130.

Figure 19:
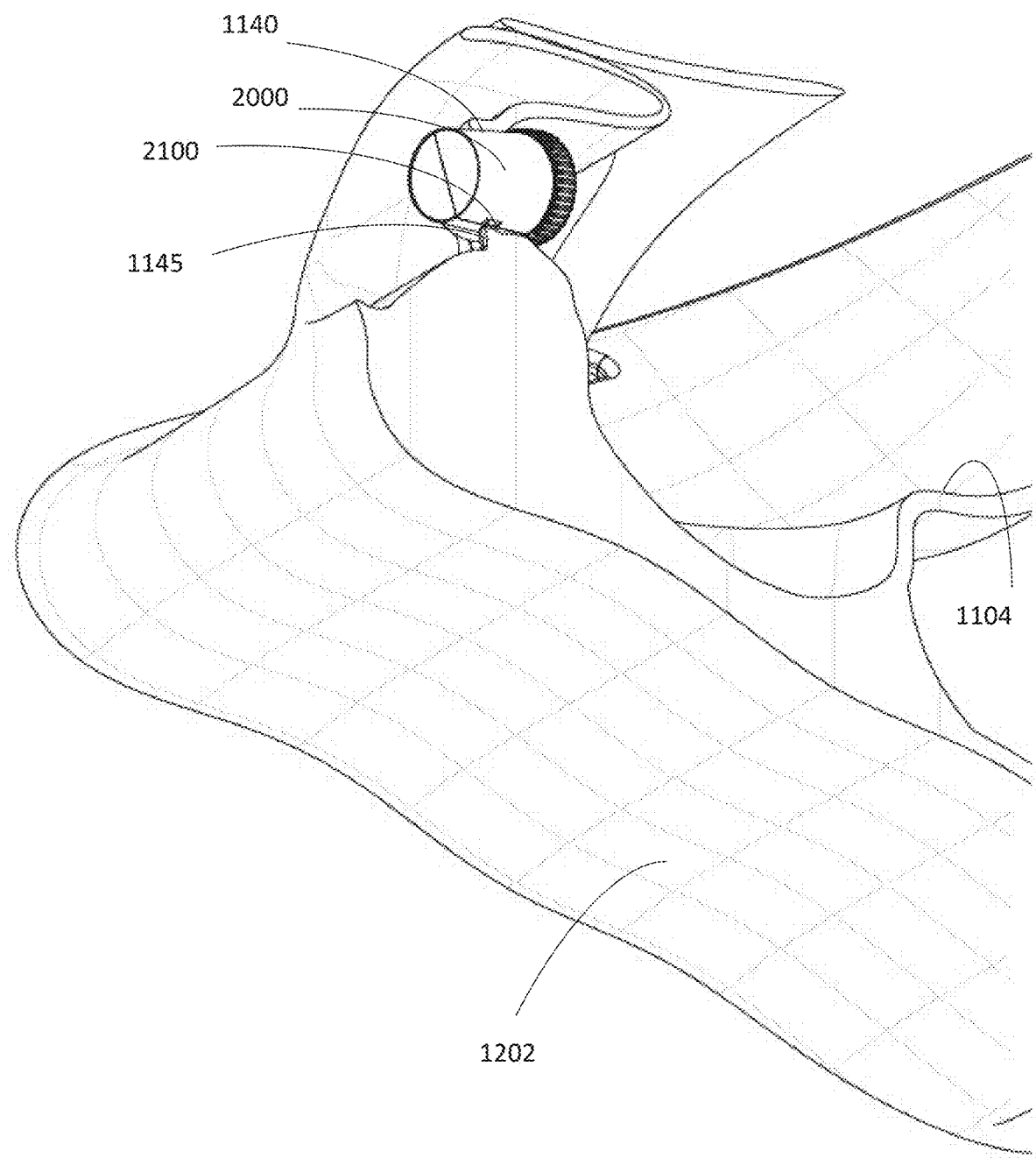
FIG. 19 is an isometric cut-away view of one form of device of the present technology and one form of cup in which a lid has been attached to the cup.
Figure 20:
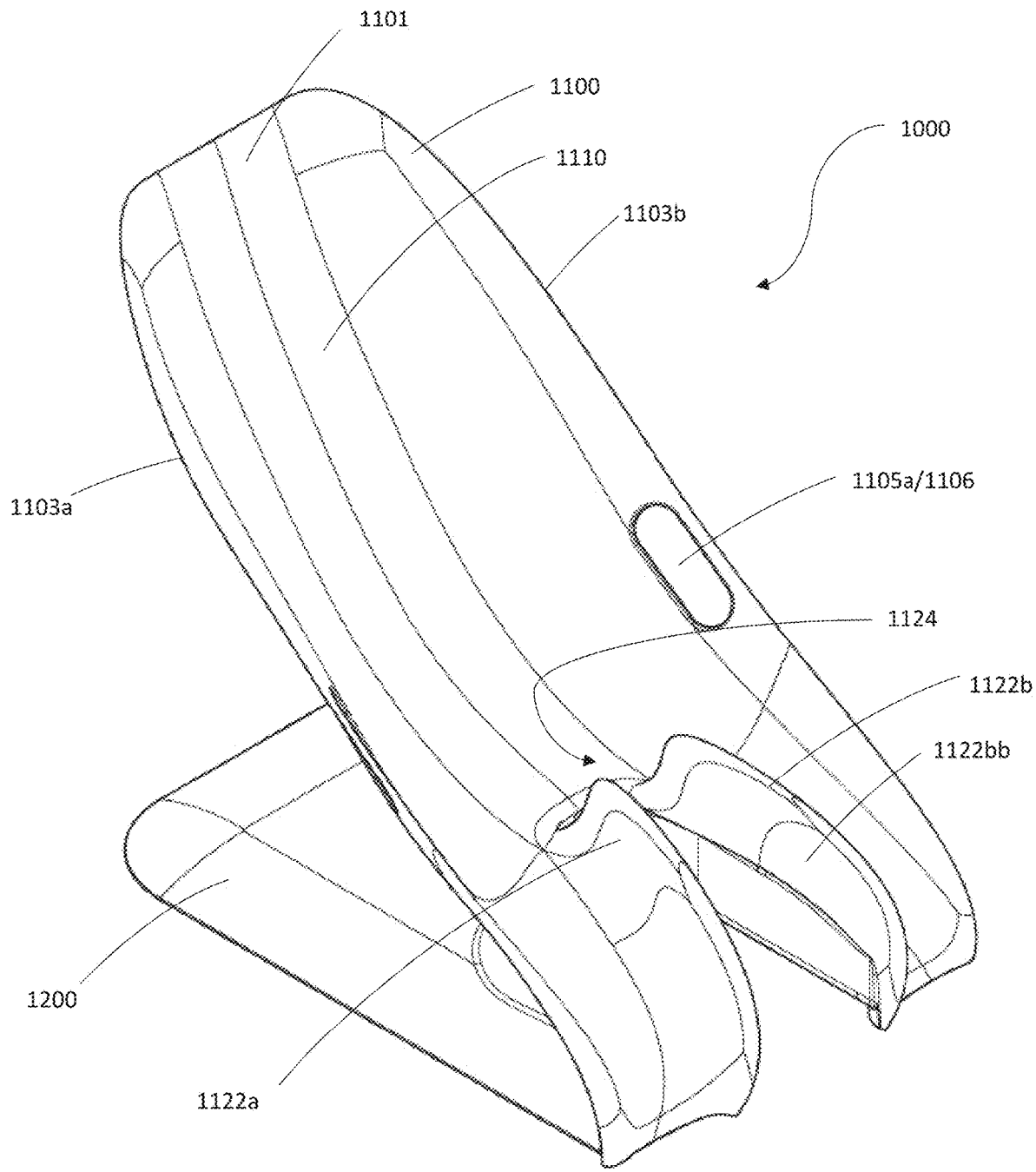
FIG. 20 is an isometric view of another form of seat for the device of the present technology, in which the collection element is separately formed to the seat and is located within a space between side walls of the saddle.
Figure 21:
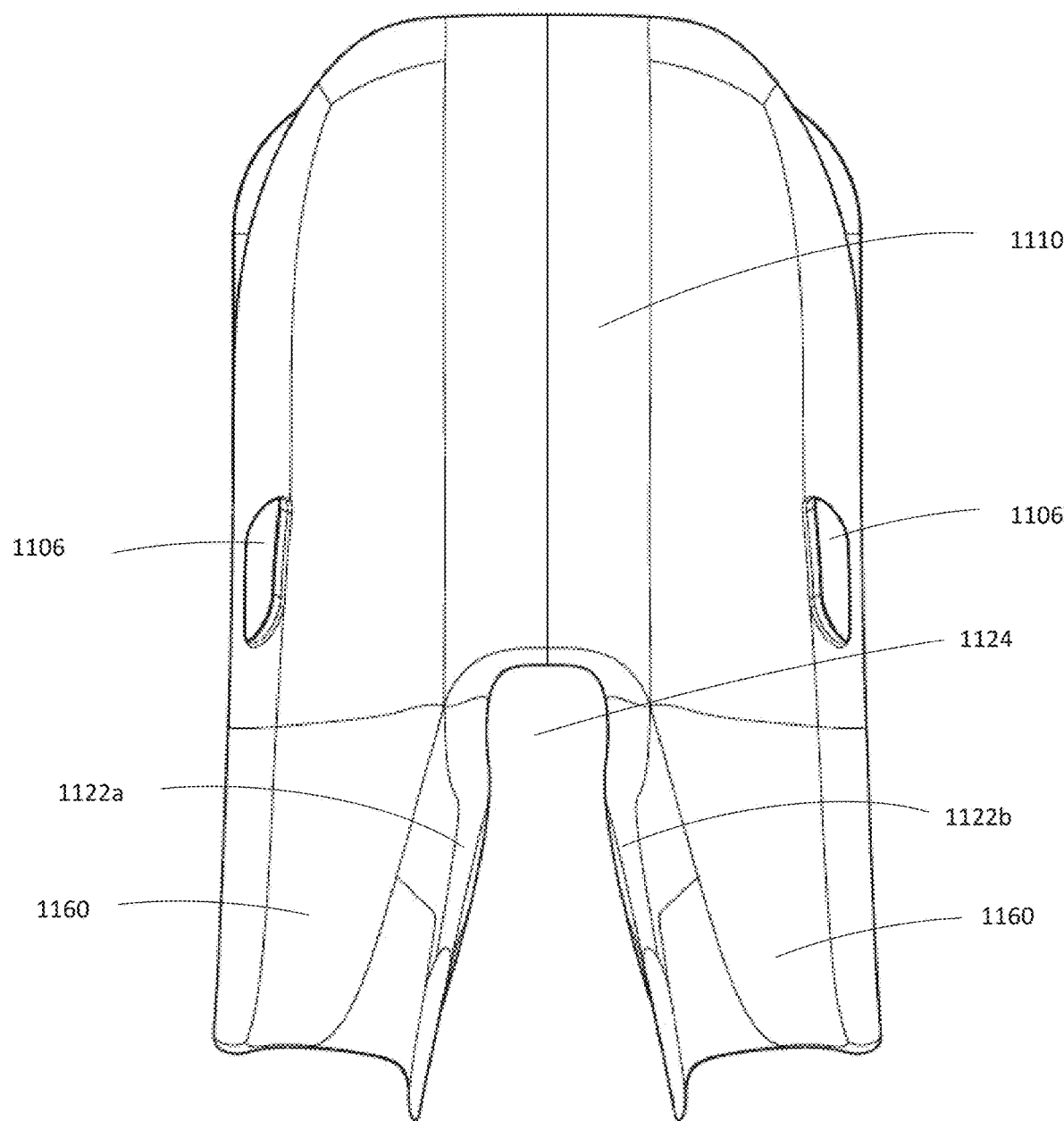
FIG. 21 is a top view of the seat of FIG. 20, showing an open saddle configuration.
Figure 22:
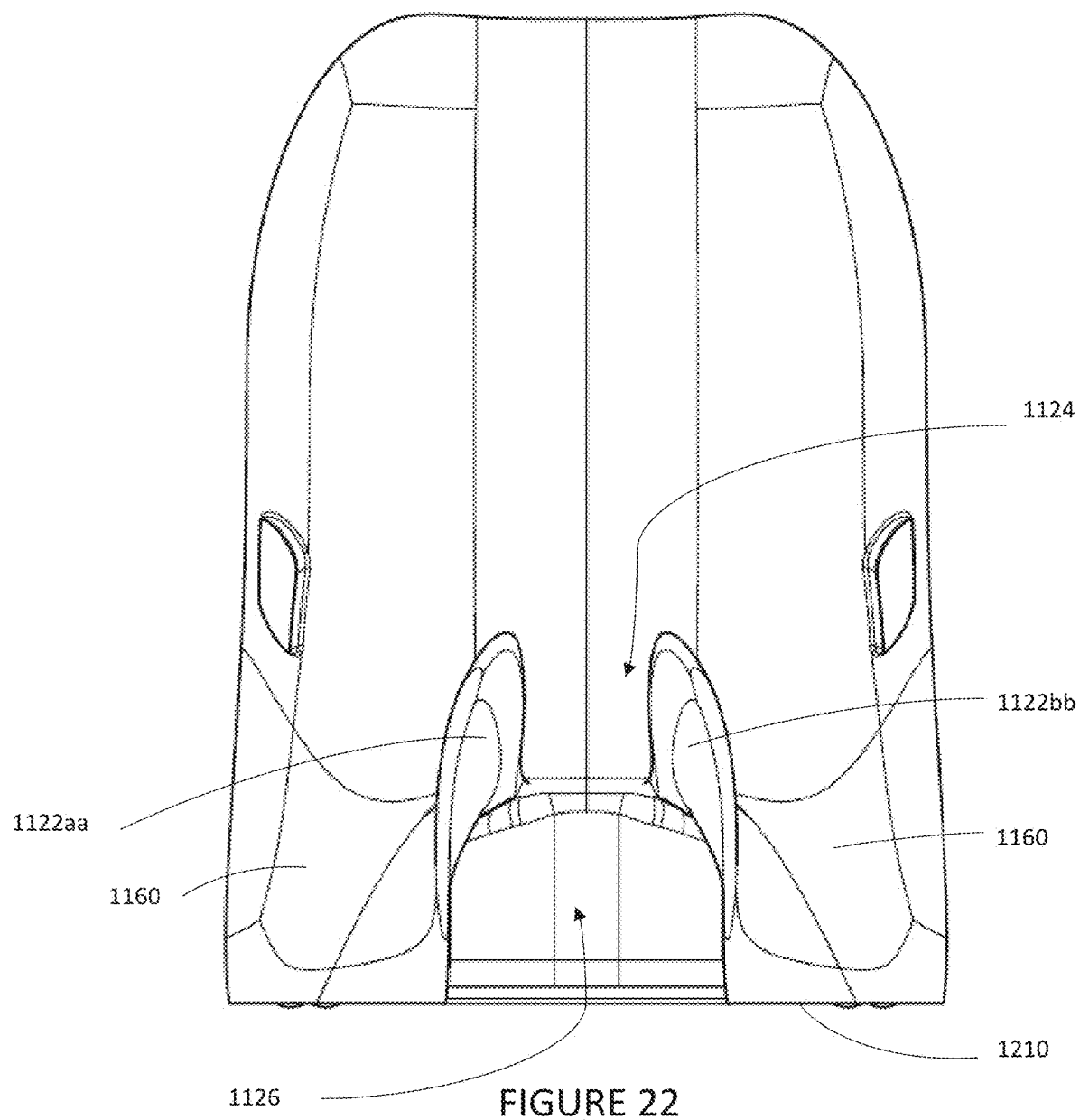
FIG. 22 is a front view of the seat of FIG. 20, showing a space between side walls of the saddle in which the collection element is locatable.
Figure 23:
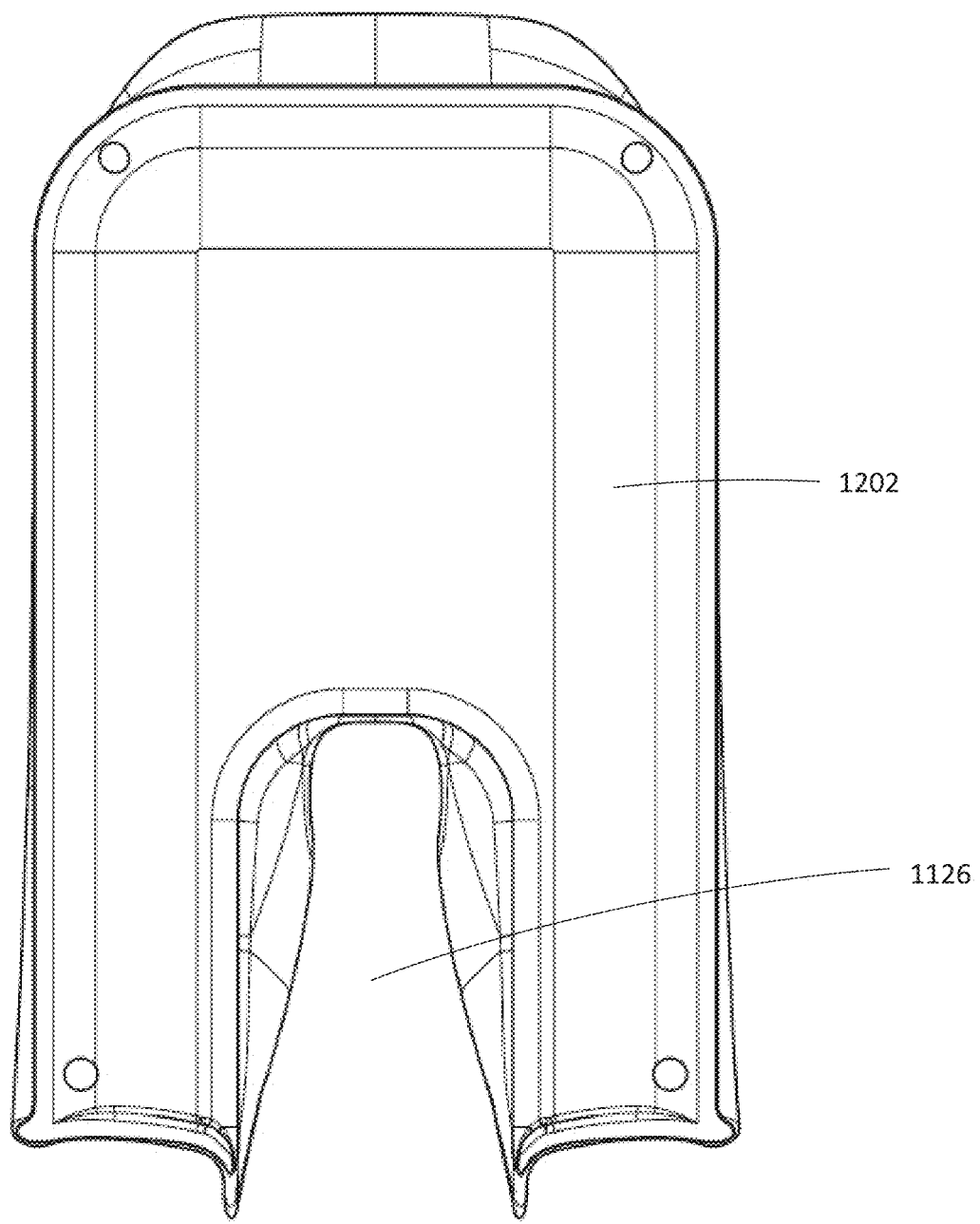
FIG. 23 is a bottom view of the seat of FIG. 20.
Figure 24:
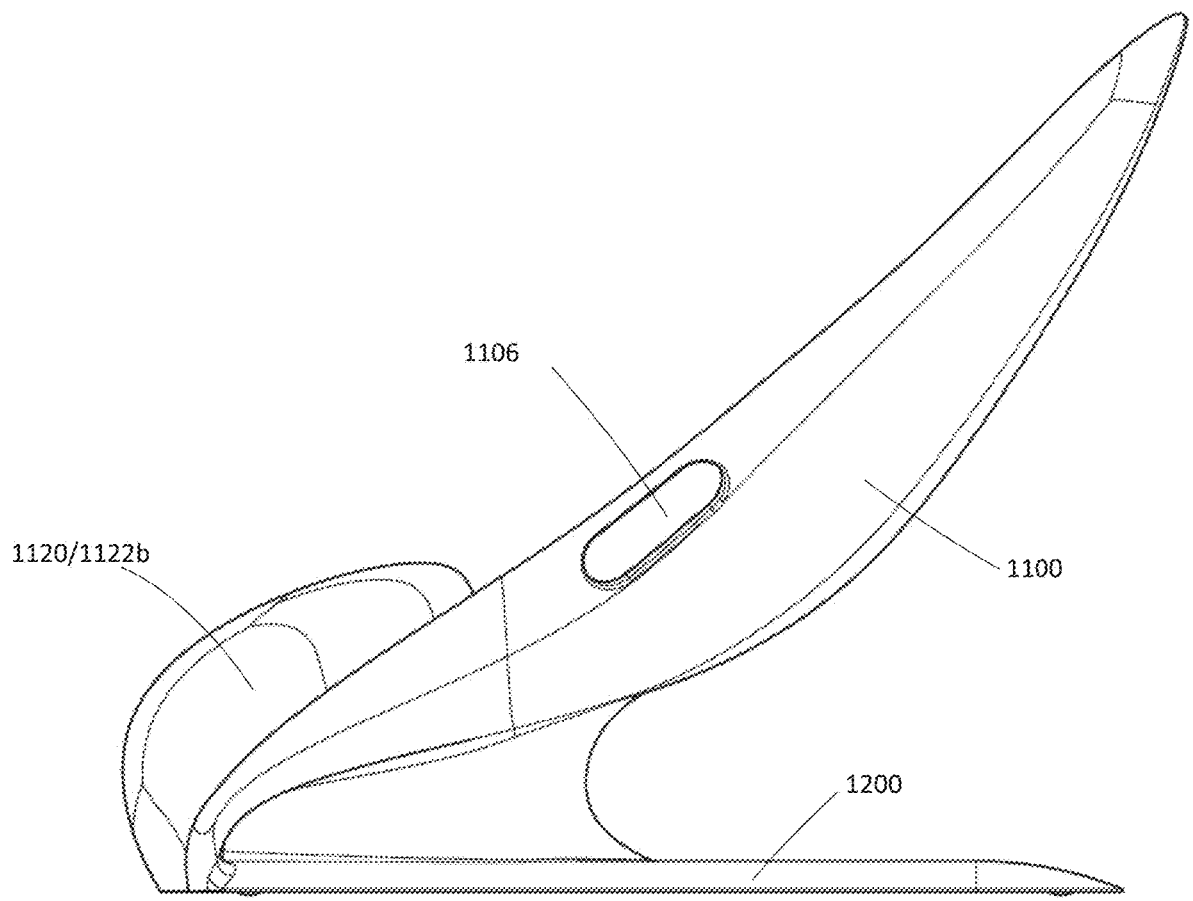
FIG. 24 is a side view of the seat of FIG. 20.

After a urine sample has been captured in the cup, a clinician may attach the lid 2200 to the cup 2000, as shown in FIG. 19, and may then retract the cup from the collection element by simply screwing the lid onto the cup and then pulling the cup out of the collection element by the lid. In this way, the clinician has a clean contact point and does not need to touch the cup or surrounding region, which may be splattered with urine. The exterior surface of the cup may comprise one or more locking features 2100 that engage with one or more complimentary locking features 1145 provided within the collection element to prevent rotation of the cup as the lid is screwed on. The locking features 2100, 1145 may be of any suitable form. For example, the collection element may comprise one or more notches for engaging with one or more projections on the exterior surface of the collection cup. Conversely, the collection element may comprise one or more projections for engaging with one or more notches provided on the exterior surface of the collection cup.

Before retrieval of the cup, the patient may be removed from the device/chair 1000. Where the patient is held by a retaining member 1170, at least one of the first and second ends of the retaining member is detached from the device 1000 before the patient is removed.

In yet another form, as shown in FIGS. 20 to 33, the device 1000 of the present technology comprises a seat comprising a seat portion 1100 and base 1200 as described above. The seat portion 1100 comprises a reclining backrest 1110, left and right sides 1103a, 1103b, and a saddle 1120 projecting from a front surface 1101 of the seat portion 1100, as previously described. The seat portion 1100 optionally comprises a hollow 1150 between the backrest 1110 and the saddle 1120 and also optionally comprises a pair of leg wells 1160, each one of the pair of leg wells 1160 extending down a respective side of the saddle 1120 and between side walls 1122a, 1122b of the saddle and sides 1103a, 1103b of the seat portion 1100, also as previously described. In some forms, the device may also comprise a retaining member to retain a patient on the seat, as described above and as shown in relation to the embodiments of FIGS. 12 to 14. In these forms, the seat portion 1100, and optionally also the saddle 1120, may comprise one or more engagement features 1105, 1125 for engaging with the retaining member 1170 to attach the retaining member to the seat, as previously described. In some forms, the seat portion 1100 may comprise a handle 1106 on each side 1103a, 1103b to enable the device 1000 to be readily lifted and relocated.

However, the embodiments of FIGS. 20 to 33 provide an alternative saddle and collection element than those of FIGS. 1 to 19. In the embodiments of FIGS. 20 to 33, the collection element 1300 is a separate component to the seat (seat portion 1100 and base 1200) and is adjustably located between the saddle side walls 1122a, 1122b. In this arrangement, as shown best in FIGS. 20 to 22, the saddle 1120 comprises a saddle opening 1124 to provide access to the collection element 1300 and collection cup 2000. The saddle 1120 also comprises a pair of spaced apart side walls 1122a, 1122b located on either side of the saddle opening 1124. A space 1126 is defined between the saddle side walls 1122a, 1122b and the collection element 1300 is adjustably locatable within the space 1126 by sliding the collection element toward or away from the saddle opening 1124.

Figure 25:
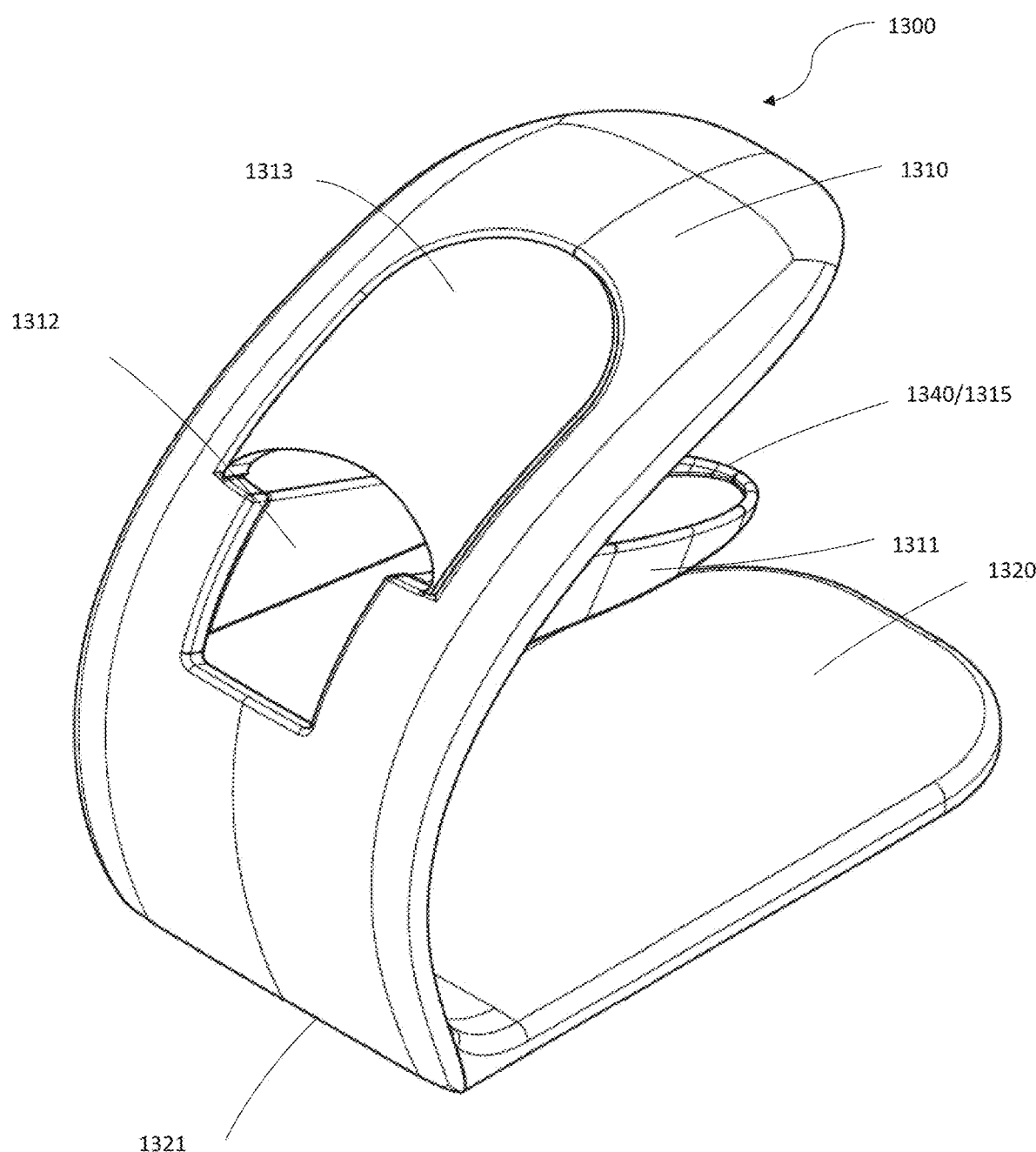
FIG. 25 is an isometric view of one form of collection element to be used with the seat of FIG. 20.

In these forms, the collection element 1300 comprises a shield 1310 that is connected to a slidable support base 1320. In some forms, the shield 1310 extends directly from the base 1320, such as from a front edge 1321 of the support base. In other forms, an intermediary component may connect the shield 1310 to the support base 1320. The shield 1310 forms a front wall of the collection element 1300 and prevents urine from spraying forward of the device 1000. In some forms, the shield 1300 is substantially curved to help retain urine overspray and to provide an aesthetically appealing and ergonomic design, as shown in FIG. 25.

A cup stand 1311 is located behind and preferably projects from a rear surface of the shield 1310. In other forms, the cup stand 1311 is supported by the support base 1320. The cup stand comprises a cup mount 1340 for receiving a sterile collection cup 2000 during use.

In some forms, the cup stand 1311 comprises a cup receiving opening 1314 for receiving at least a portion of a sterile collection cup 2000 therein. The cup receiving opening 1314 is defined by a rim 1315 that provides a cup mount 1340.

The cup receiving opening 1314 is shaped and dimensioned to receive at least a portion of a urine collection cup 2000. For example, the cup receiving opening may be circular to receive a collection cup comprising a substantially circular periphery, or the cup receiving opening may be oblong to receive a collection cup comprising a substantially oblong periphery. In some forms, the collection cup 2000 may comprise a varying diameter or width along the height of the cup, especially if the cup is tapered to be narrower at the bottom and wider at the top. The cup receiving opening 1314 typically has a diameter or width that is larger than the diameter or width of a lower portion of the cup and that is smaller than the diameter or width of an upper portion of the cup 2000. In this configuration, the lower portion of the cup 2000 may be inserted through the opening 1314 until the diameter or width of the cup 2000 substantially corresponds with the diameter or width of the opening 1314. At this point, an outer surface of the cup 2000 or a projecting lip of the cup may contact the rim 1315 of the opening 1131. For example, a projecting lip of the cup 2000 may rest above the rim 1315 with the remainder of the cup extending through the cup receiving opening 1314. Alternatively, an outer side surface of the cup 2000 may press against an inner surface of the rim 1315 to suspend the cup within the cup receiving opening 1314. The wider upper portion of the cup 2000 extends above the opening 1314 and prevents the cup 2000 from moving further down into the opening 1314. In effect, the rim 1315 engages with the urine collection cup 2000 to hold the cup within the collection element 1130. In this way, the collection cup 2000 is suspended within the cup receiving opening 1314 and the rim 1315 provides a mount 1340 for the cup 2000. Optionally, the cup stand may comprise one or more side walls 1311*b* to help prevent any urine spills from dribbling off the cup stand. The side wall(s) 1311*b* may partially or fully surround the rim 1315.

Alternatively, the cup stand 1311 comprises a bottom surface that forms the cup mount 1340 and the collection cup 2000 sits on bottom surface. Optionally, the cup stand may comprise one or more side walls to help prevent any urine spills from dribbling off the cup stand. The side wall(s) may partially or fully surround the bottom surface.

Figure 26:
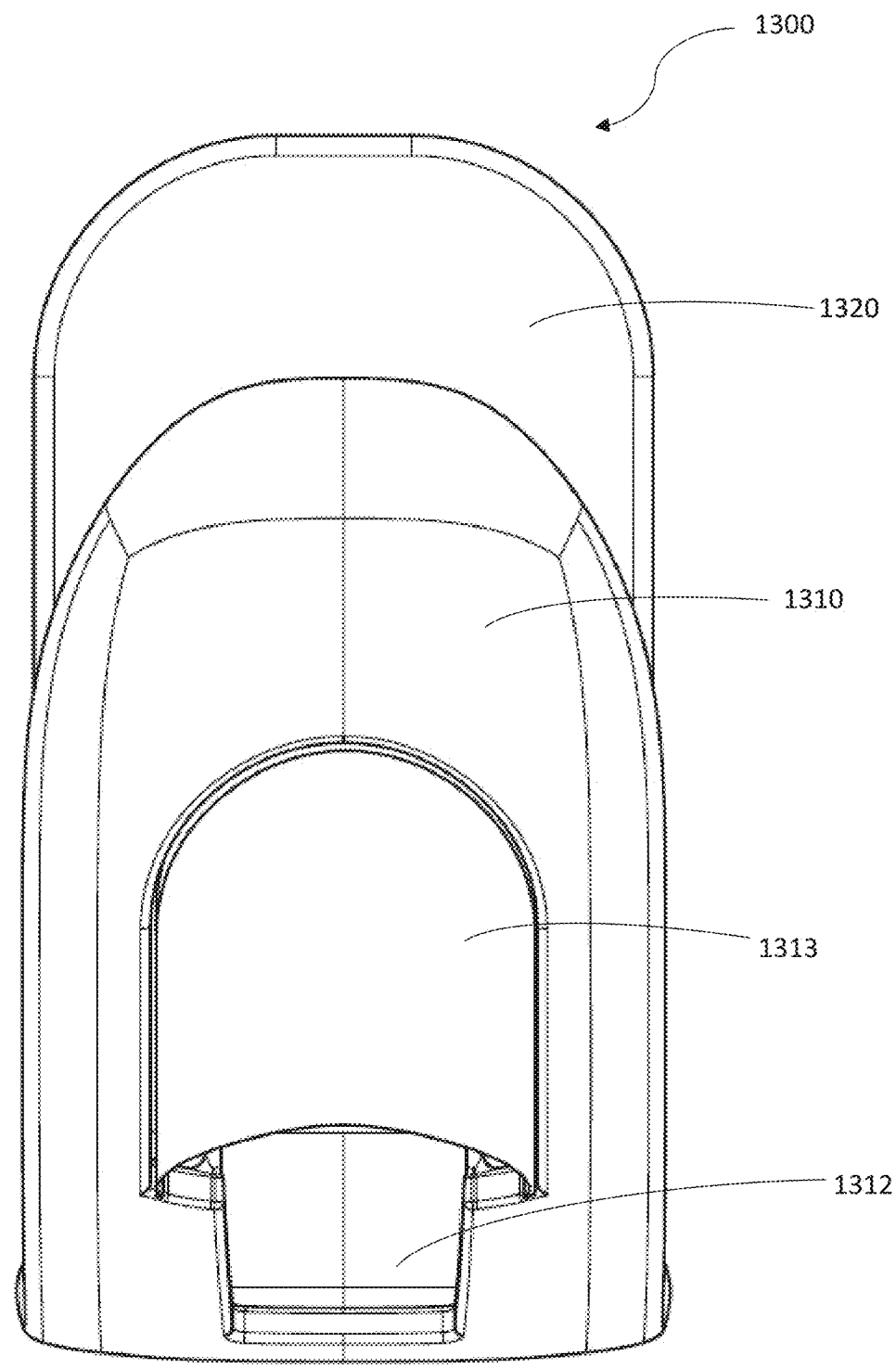
FIG. 26 is a top view of the collection element of FIG. 25.
Figure 27:
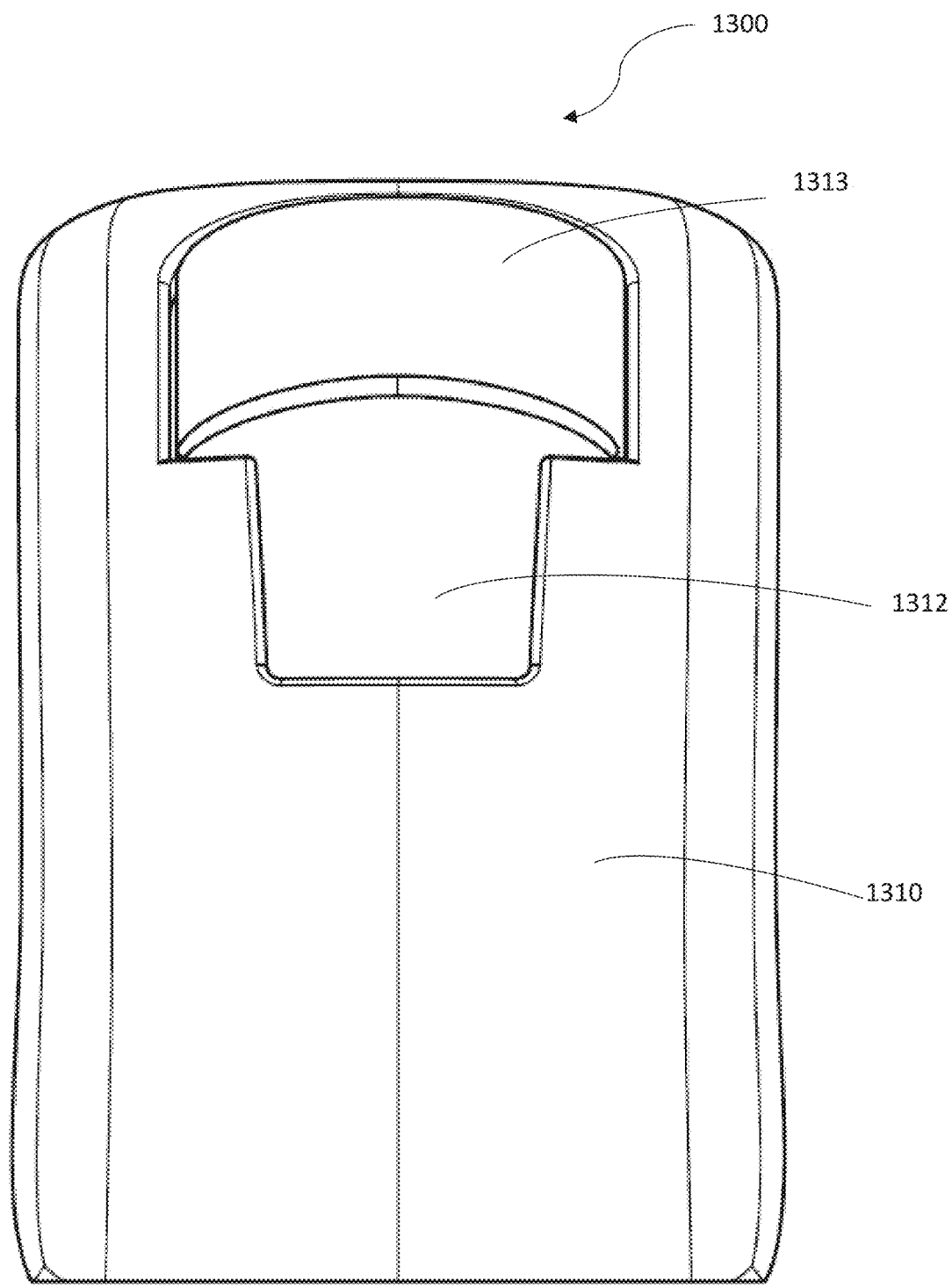
FIG. 27 is a front view of the collection element of FIG. 25.
Figure 28:
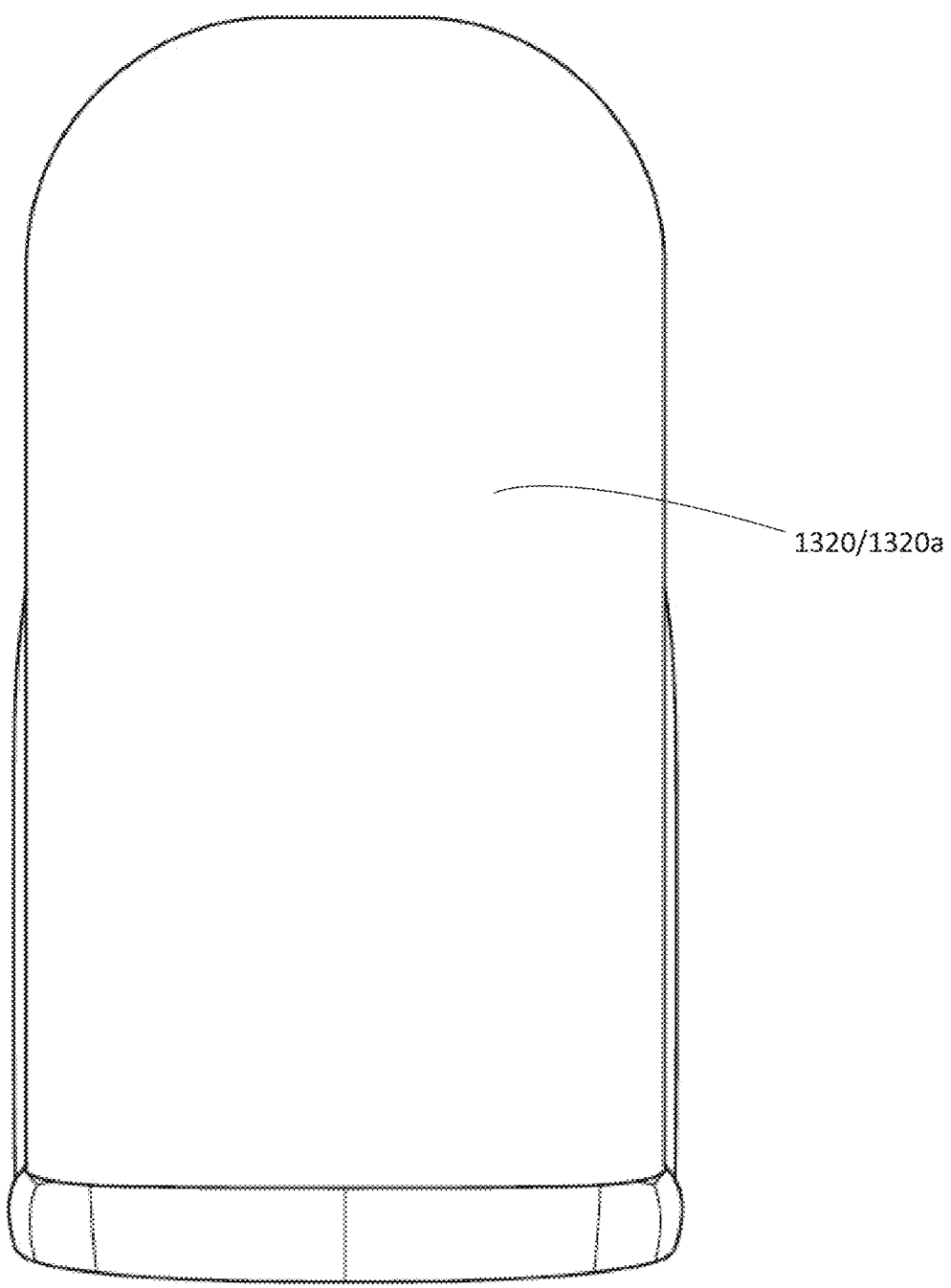
FIG. 28 is a bottom view of the collection element of FIG. 25.
Figure 29:
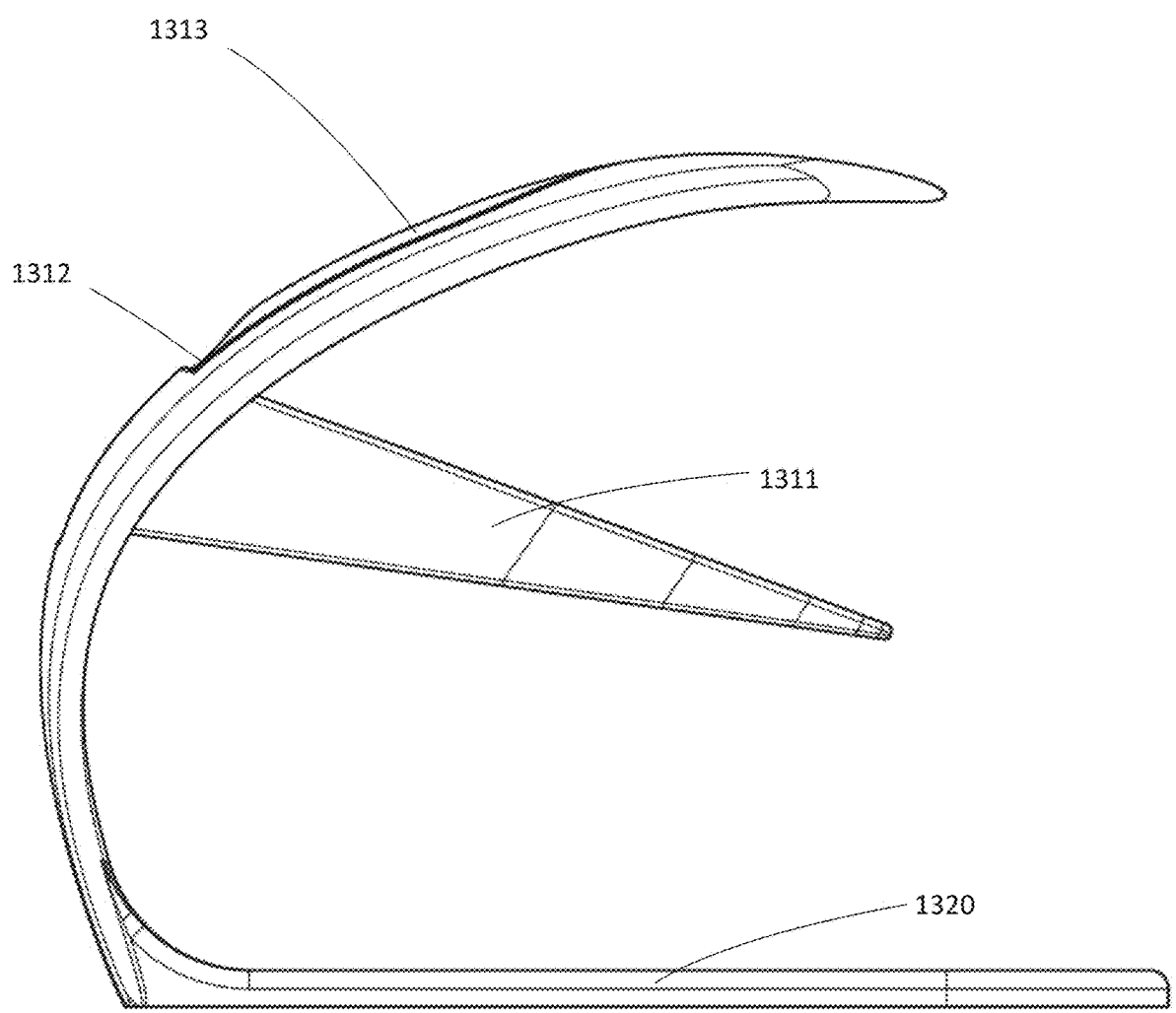
FIG. 29 is a side view of the collection element of FIG. 25 showing the cup mount projecting from the shield of the collection element.
Figure 29A:
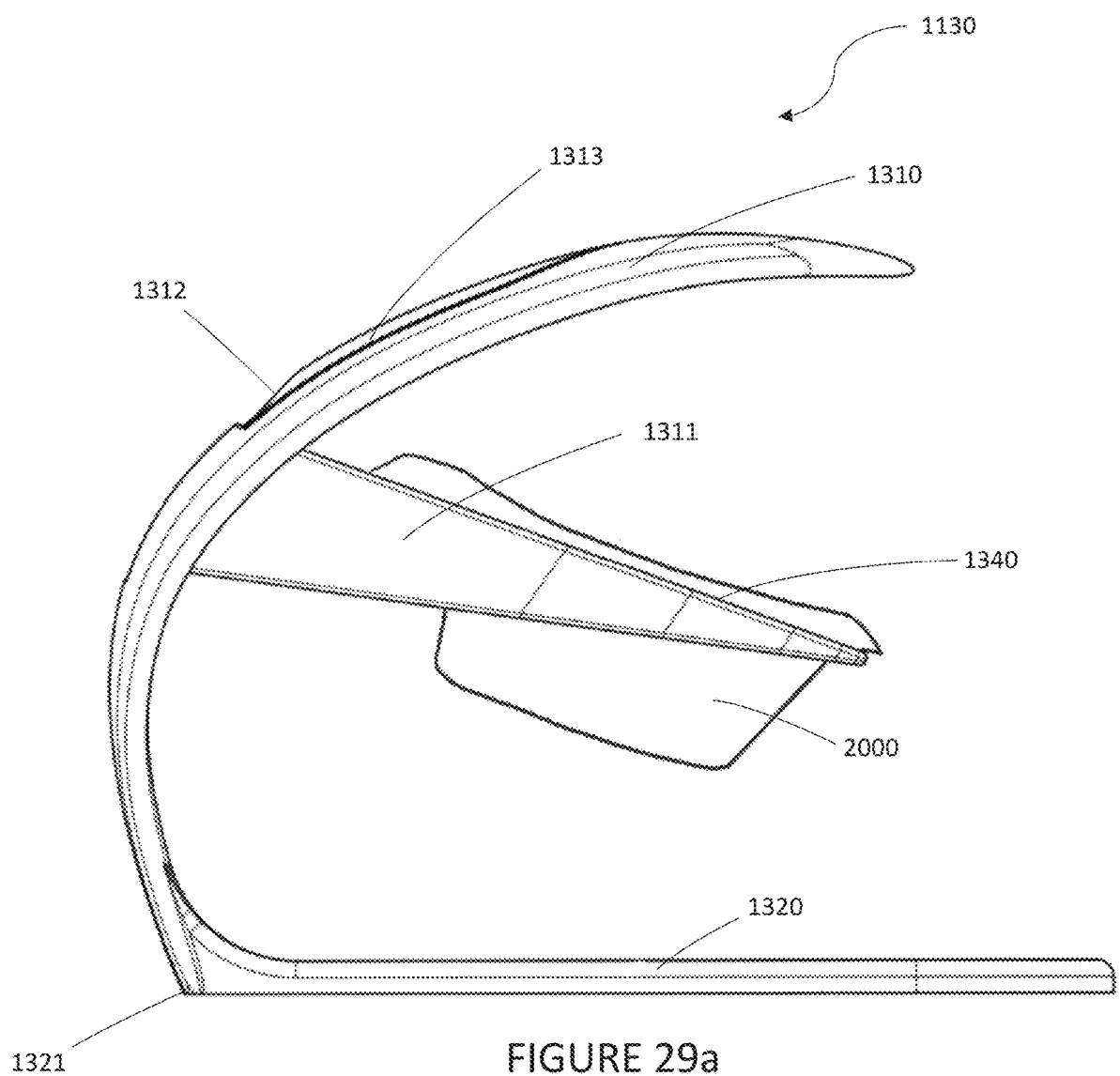
FIG. 29a a side view of the collection element of FIG. 25 holding a collection cup within the cup mount.

In some forms, as shown in FIGS. 25 to 27, the shield 1310 comprises an access opening 1312 through which the collection cup 2000 can be inserted or removed from the collection element 1300, even when the collection element is in situ.

Figure 30:
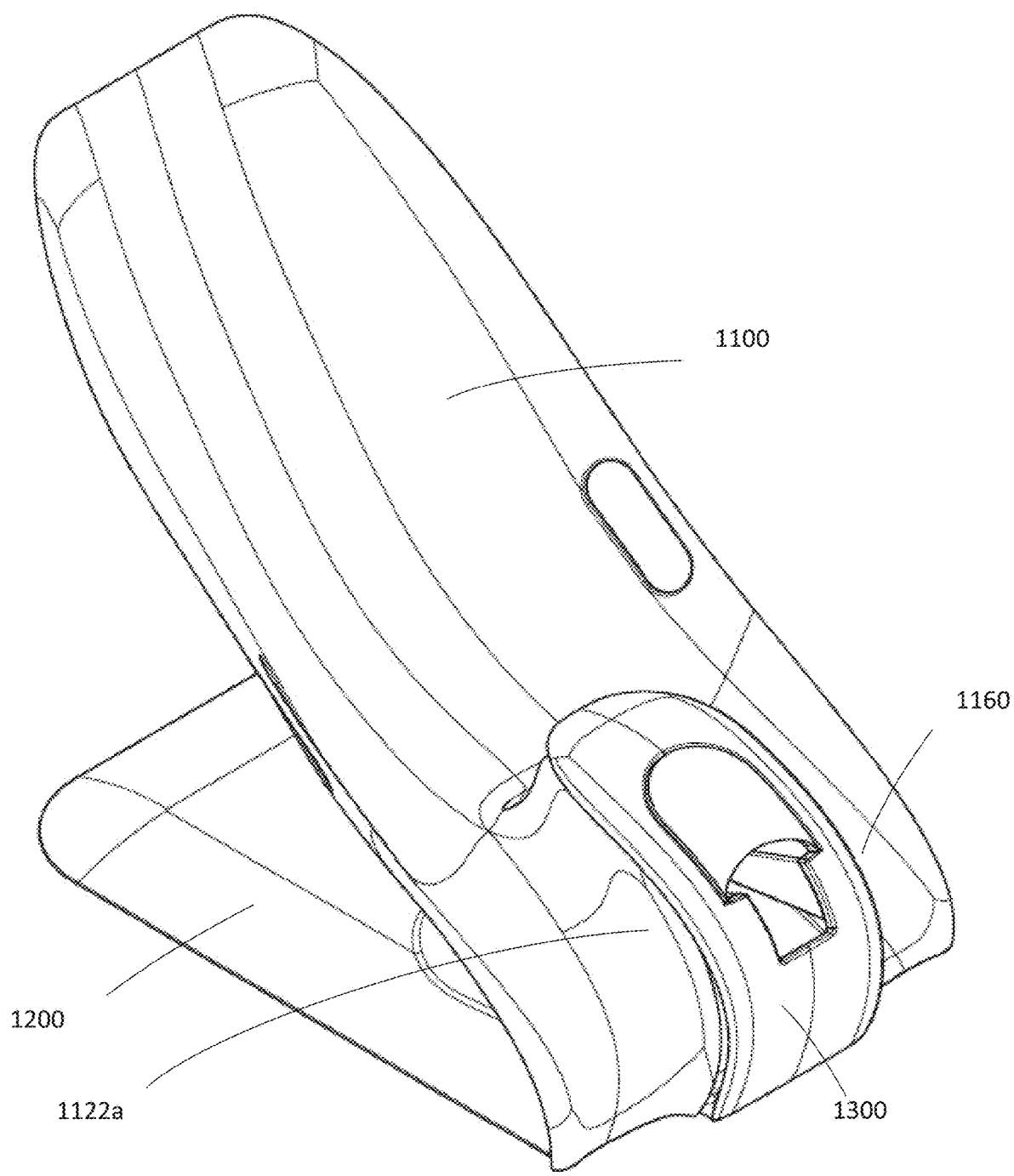
FIG. 30 is an isometric view of the seat of FIG. 20 and the collection element of FIG. 25 in combination.
Figure 30A:
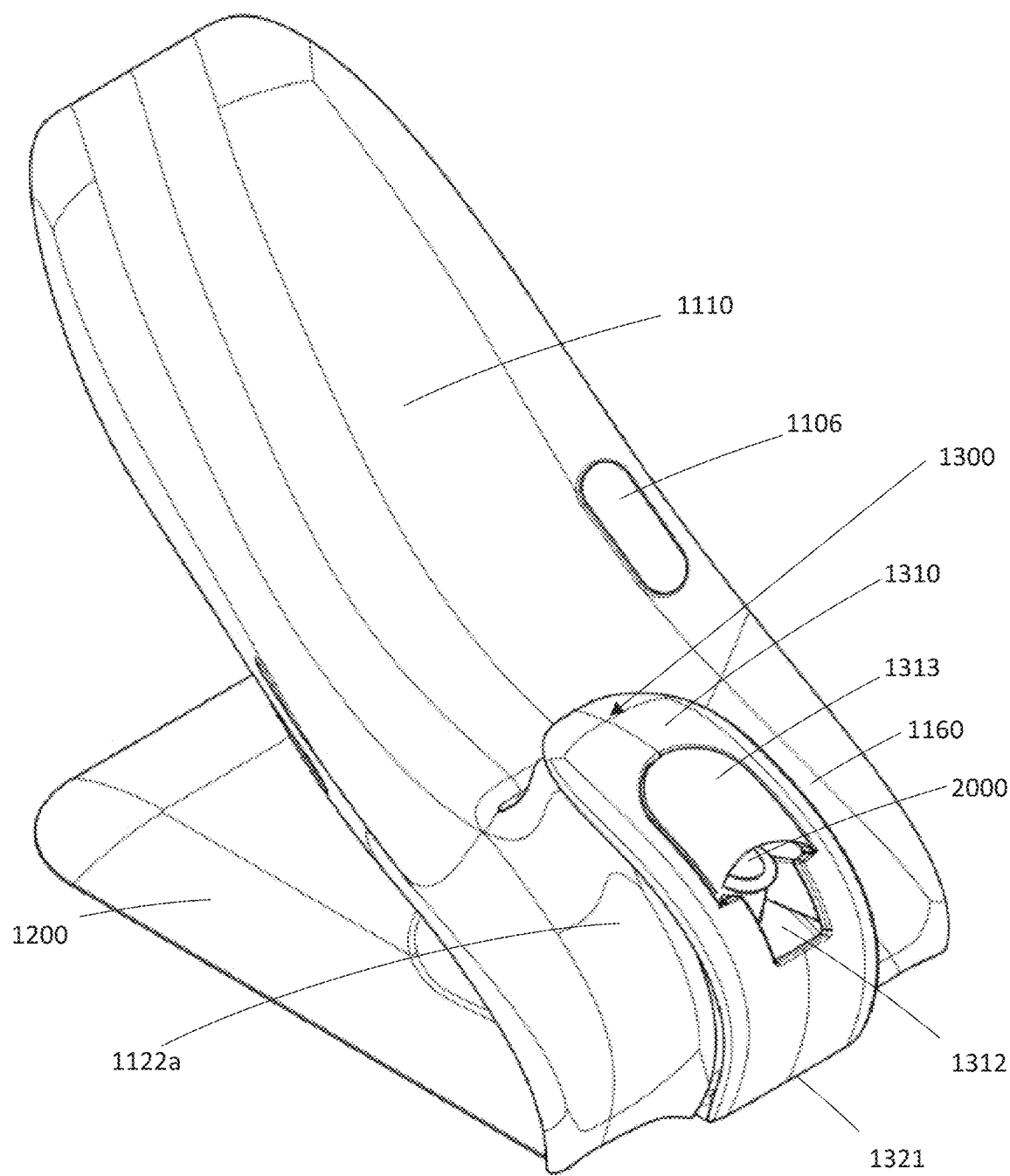
FIG. 30a is an isometric view of the assembly of FIG. 30 and in which a collection cup is mounted in the collection element.
Figure 31:
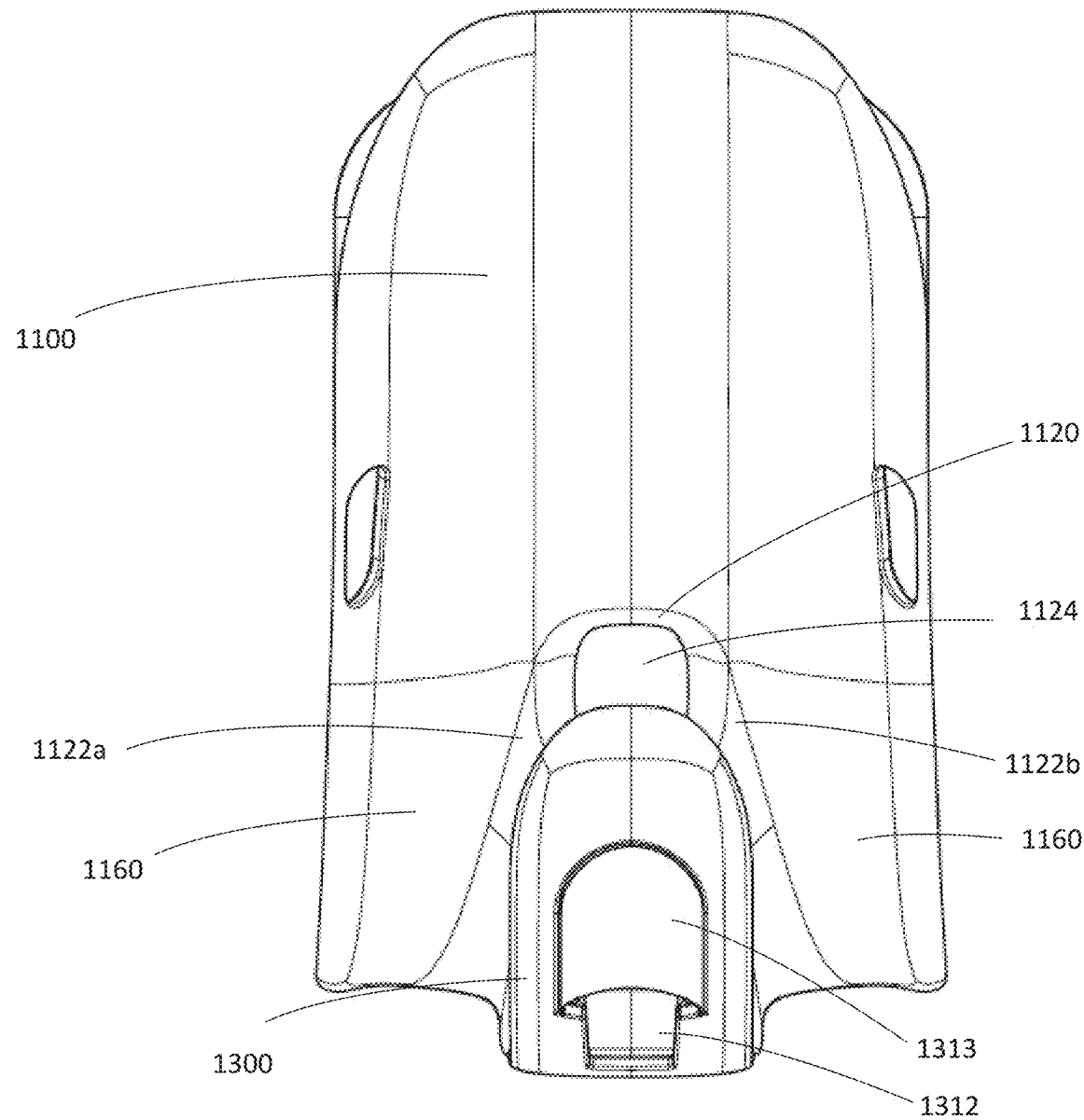
FIG. 31 is a top view of the assembly of FIG. 30 and in which the collection element is partially inserted between the side walls of the saddle.
Figure 32:
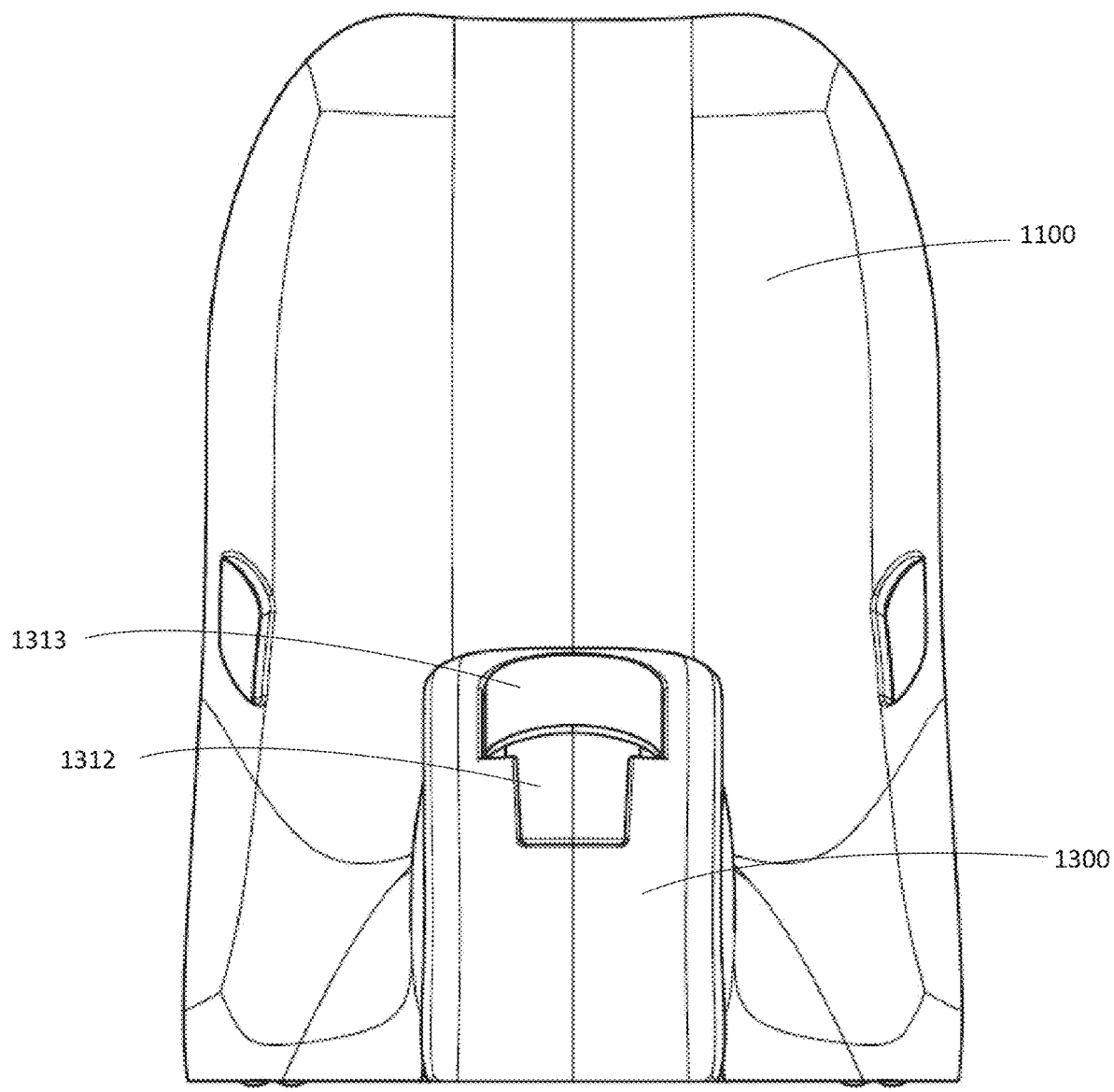
FIG. 32 is a front view of the assembly of FIG. 30.
Figure 33:
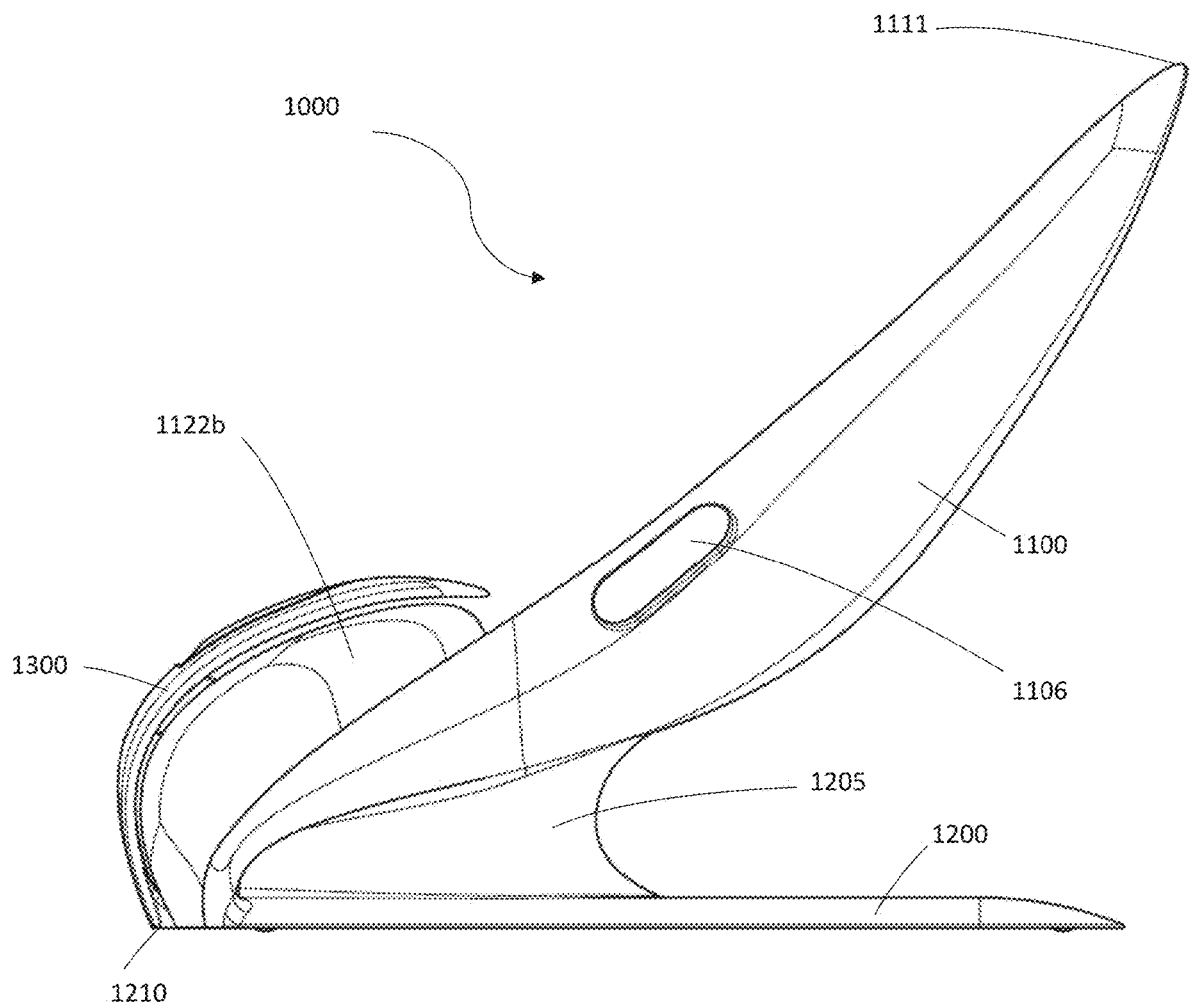
FIG. 33 is a side view of the assembly of FIG. 30 and in which the collection element is fully inserted between the side walls of the saddle.

In some forms, as shown in FIGS. 25 to 27 and 29, the shield 1310 comprises a transparent screen 1313 through which it is possible to see whether a urine sample has been received within the collection cup 2000. In some forms, a transparent screen is provided on a curved shield 1310 above an access opening 1312, as shown in FIGS. 25 and 30*a*.

In some forms, the space 1124 between the saddle side walls 1122*a*, 1122*b* is wider toward the front of seat portion 1100 and the collection element 1300 is also wider at the front of the element, providing a substantially wedge-shaped element 1300. This arrangement may make it easier to maneuver the slidable collection element 1300 into position between the saddle walls 112*a*, 112*b* and to remove the collection element.

To use the device 1000 and collection element 1300 of FIGS. 20 to 30*a*, a patient is positioned on the seat portion 1100 of the device. A sterile collection cup 2000 is located on the cup mount 1340, such as by positioning the cup within a cup receiving opening 1314 of the cup stand 1311 or by resting the bottom of the cup 2000 on the bottom surface of the cup stand, as the case may be. The cup mount 1340 may be accessed through an access opening 1312 or from a rear or side of the collection element 1300. The collection cup 2000 may be placed in the cup mount 1340 before or after the patient is positioned on the seat portion 1100. The collection element 1300 is slid into position between the saddle walls 1122*a*, 1122*b* and is located at a distance from the saddle opening 1124 at which the clinician believes that the cup 2000 will receive a flying stream of urine from the patient. The collection element 1300 may be located between the saddle walls before or after the patient is positioned on the seat portion 1100. A clinician then waits for the patient to urinate. Where the collection element 1300 comprises a transparent screen 1313, the clinician is able to monitor the collection cup 2000 through the screen 1313 to see whether the patient is urinating and to see whether the cup 2000, and therefore the collection element 1300, is in the correct position to catch a flying stream of urine. The clinician can adjust the position of the cup by sliding the collection element 1300 toward or away from the saddle opening 1124. The shield 1310 of the collection element 1300 and inner side walls 1122*aa*, 1122*bb* of the saddle 1120 form an enclosure to prevent urine spray outside the device 1000. After a urine sample is received in the collection cup 2000, the cup may be removed through the access opening 1312 or by sliding the collection element 1300 away from the seat portion 1100 and removing the cup from the rear or side of the collection element. A lid may be applied to the cup 2000, if the cup is configured to receive a lid, before or after removing the cup from the collection element 1300. The patient may then be removed from the seat portion 1100.

Because of the sliding nature of the collection element 1300, the device 1000 is best suited for use on a flat surface, such as a bench, table, floor, or the like. As above, the bottom surface 1202 of the device may comprise a non-slip surface, but it is preferred that a bottom surface 1320*a* of the collection element 1300 is freely slidable.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the scope of the invention and without diminishing its attendant advantages. It is therefore intended that such changes and modifications be included within the scope of the invention.

I claim:

1. A urine collection device adapted to collect a sterile urine sample from a patient, the device comprising a seat portion supported by a seat base, and a collection element to collect the sterile urine sample from the patient,
   wherein the seat portion comprises:
      a rearwardly reclining backrest adapted for the patient to recline on his or her back, during use of the device;
      a hollow, to collect fecal matter and spilled urine; and
      a saddle that projects from the seat portion, the saddle being adapted to be located between the patient's legs and in front of the patient's genitals during use;
   wherein the saddle comprises a saddle opening and a pair of spaced apart side walls located on either side of the saddle opening and defining a space between the side walls of the saddle, the saddle opening providing fluid access to the space and the collection element;
   wherein the collection element comprises a shield connected to a slidable support base, the shield being adapted to prevent urine spraying forward of the device, the collection element comprising a cup mount to locate a removeable and replaceable sterile urine collection cup to collect a flying stream of urine from the patient;

wherein the collection element is slidably located between the side walls of the saddle to adjust the distance of the collection element, and the collection cup, relative to the saddle opening in order to collect the flying stream of urine directly from the patient; and wherein the hollow is located between the backrest and the saddle and is at least partially defined by a shelf region that surrounds at least a portion of the hollow, the shelf region being adapted to allow at least a portion of the patient's buttocks to rest on the shelf region, with the patient's anus located above the hollow, during use.

2. The urine collection device of claim 1, wherein the collection element comprises a cup receiving opening defined by a rim, the cup receiving opening being shaped and dimensioned to receive at least a portion of the removeable and replaceable urine collection cup within the cup receiving opening to hold the cup within the collection element.

3. The urine collection device of claim 2, wherein the collection element comprises one or more side walls that slope toward the cup receiving opening.

4. The urine collection device of claim 1, wherein the hollow comprises a bottom surface that is at least partially defined by one or more curved side walls to collect the fecal matter and urine overflow.

5. The urine collection device of claim 1, wherein the backrest comprises a central portion located between two side portions, each of the side portions terminating at a respective left or right side of the seat portion, and wherein the backrest is angled or curved between the left and right sides so that the central portion of the backrest is rearward of the left and right sides.

6. The urine collection device of claim 1, wherein the seat portion comprises a pair of leg wells to receive a patient's legs therein, each of the leg wells extending along the seat portion on either side of the saddle.

7. The urine collection device of claim 1, wherein a cup stand projects from a rear surface of the shield and wherein the cup mount is provided on the cup stand.

8. The urine collection device of claim 1, wherein the seat base comprises a pair of spaced apart, arcuate channels that extend from a left side of the seat base to a right side of the seat base to position the seat base on the thighs of an adult when the device is in use.

9. The urine collection device of claim 1, wherein the rearwardly reclining backrest is oriented at an acute angle relative to the seat base.

10. The urine collection device of claim 1 and further comprising a retaining member that spans across the seat portion and is adapted to retain the patient on the device, wherein the retaining member comprises a substantially T-shaped three-point harness comprising a first end that attaches to one side of the backrest, a second end that attaches to the other side of the backrest, and a third end that attaches to the saddle.

11. The urine collection device of claim 10, wherein the seat portion and at least one of the ends of the retaining member each comprise at least one engagement feature to detachably attach the retaining member to the seat portion.

12. The urine collection device of claim 11, wherein the engagement feature comprises a magnetic region such that the retaining member detachably attaches to the seat portion by a magnetic connection.

13. The urine collection device of claim 12, wherein at least one of the first and second ends of the retaining member comprises a magnetic region and wherein a rear surface of the seat portion comprises a magnetic region to which the retaining member may be detachably attached.

14. The urine collection device of claim 12, wherein at least one of the first and second ends of the retaining member is insertable through an opening provided in a respective side of the seat portion and is detachably attachable to the magnetic region on the rear surface of the seat portion.

15. The urine collection device of claim 12, wherein the retaining member comprises silicone and one or more magnets are located beneath an outer silicone surface of the retaining member.

16. The urine collection device of claim 12, wherein the magnetic region of the seat portion engagement feature, or the saddle, or both, comprises one or more magnets that are either embedded within the respective seat portion, or saddle, or both or that are covered or over-molded with a polymer.

17. The urine collection device of claim 10, wherein the third end of the harness comprises a magnetic region and the saddle comprises a magnetic region to attach to the third end.

* * * * *